United States Patent
Guillonneau et al.

US011191807B2

(10) Patent No.: US 11,191,807 B2
(45) Date of Patent: Dec. 7, 2021

(54) LEBECETIN, A C-TYPE LECTIN, AS NEOVASCULARIZATION INHIBITOR

(71) Applicants: SORBONNE UNIVERSITE, Paris (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR); INSTITUT PASTEUR DE TUNIS, Tunis (TN)

(72) Inventors: Xavier Guillonneau, Boulogne Billancourt (FR); Fadoua Montassar, Paris (FR); Naziha Marrakchi, Ariana (TN); Erij Messadi, Tunis (TN); Florian Sennlaub, Paris (FR); José-Alain Sahel, Paris (FR)

(73) Assignees: SARBONNE INIVERSIÉ, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MEDICALE), Paris (FR); INSTITUT PASTEUR DE TUNIS, Tunis (TN)

( * ) Notice: Subject to any disclaimer, the term of this patent is extended or adjusted under 35 U.S.C. 154(b) by 0 days.

(21) Appl. No.: 16/468,305

(22) PCT Filed: Dec. 12, 2017

(86) PCT No.: PCT/EP2017/082482
§ 371 (c)(1),
(2) Date: Jun. 11, 2019

(87) PCT Pub. No.: WO2018/108945
PCT Pub. Date: Jun. 21, 2018

(65) Prior Publication Data
US 2019/0298797 A1 Oct. 3, 2019

(30) Foreign Application Priority Data

Dec. 12, 2016 (EP) .................................... 16306661

(51) Int. Cl.
| *A61K 38/17* | (2006.01) |
| *C12N 15/86* | (2006.01) |
| *C07K 14/46* | (2006.01) |
| *C07K 14/705* | (2006.01) |
| *A61K 38/18* | (2006.01) |
| *A61P 27/02* | (2006.01) |
| *A61P 35/00* | (2006.01) |

(52) U.S. Cl.
CPC ...... *A61K 38/1703* (2013.01); *A61K 38/1866* (2013.01); *A61P 27/02* (2018.01); *A61P 35/00* (2018.01); *C07K 14/46* (2013.01); *C07K 14/7056* (2013.01); *C12N 15/86* (2013.01)

(58) Field of Classification Search
CPC . A61K 38/1703; A61K 38/1866; A61P 27/02; A61P 35/00; C07K 14/46; C07K 14/7056; C12N 15/86
See application file for complete search history.

(56) References Cited

U.S. PATENT DOCUMENTS

2011/0166072 A1* 7/2011 Chuang .................. C07K 14/46
514/15.2

FOREIGN PATENT DOCUMENTS

WO    WO 2012/154894    11/2012

OTHER PUBLICATIONS

P.G. Corrie,Targeting angiogenesis in melanoma: prospects for the future, Ther Adv Med Oncol (2010) 2(6) 367380.*
Sameh Sarray, Lebecetin, a C-Lectin Protein from the Venom of Macrovipera lebetina That Inhibits Platelet Aggregation and Adhesion of Cancerous Cells, Haemostasis 2001;31:173-176.*
Balaratnasingam, C. et al. "Aflibercept: a review of its use in the treatment of choroidal neovascularization due to age-related macular degeneration" *Clinical Ophthalmology*, 2015, pp. 2355-2371, vol. 9.
Egan, C. et al. "The United Kingdom Diabetic Retinopathy Electronic Medical Record Users Group, Report 1: baseline characteristics and visual acuity outcomes in eyes treated with intravitreal injections of ranibizumab for diabetic macular oedema" *British Journal of Ophthalmology*, Jan. 2017, pp. 75-80, vol. 101, No. 1.
Ishikawa, M et al. "Future Therapies of Wet Age-Related Macular Degeneration" *Journal of Ophthalmology*, 2015, pp. 1-11, Article ID 138070.
Jebali, J. et al. "C-type lectin protein isoforms of *Macrovipera lebetina*: cDNA cloning and genetic diversity" *Toxicon*, 2009, pp. 228-237, vol. 53, No. 2.
Jebali, J. et al. "Expression of a Functional Recombinant C-Type Lectin-Like Protein Lebecetin in the Human Embryonic Kidney Cells" *Biotechnolology Progress*, 2012, pp. 1560-1565, vol. 28, No. 6.

(Continued)

*Primary Examiner* — James H Alstrum-Acevedo
*Assistant Examiner* — Erinne R Dabkowski
(74) *Attorney, Agent, or Firm* — Saliwanchik, Lloyd & Eisenschenk

(57) ABSTRACT

The present invention relates to lebecetin, a functional variant or fragment thereof, for use as neovascularization inhibitor, in particular in the treatment of neovascular diseases such as ocular diseases, cancers or inflammatory disorders with a neovascular component.

18 Claims, 9 Drawing Sheets
(8 of 9 Drawing Sheet(s) Filed in Color)
Specification includes a Sequence Listing.

(56) References Cited

OTHER PUBLICATIONS

Jebali, J. et al. "Lebecin, a new C-type lectin like protein from *Macrovipera lebetina* venom with anti-tumor activity against the breast cancer cell line MDA-MB231" *Toxicon*, 2014, pp. 16-27, vol. 86.

Montassar, F. et al. "Lebecetin, a C-type lectin, inhibits choroidal and retinal neovascularization" *The FASEB Journal*, Mar. 2017, pp. 1107-1119, vol. 31, No. 3, Supplementary Figures pp. 1-2.

Pilorget, A. et al. "Lebectin, a *Macrovipera lebetina* Venom-Derived C-type Lectin, Inhibits Angiogenesis Both In Vitro and In Vivo" *Journal of Cellular Physiology*, 2007, pp. 307-315, vol. 211, No. 2.

Sarray, S. et al. "Lebecetin, a potent antiplatelet C-type lectin from *Macrovipera lebetina* venom" *Biochimica et Biophysica Acta*, 2003, pp. 30-40, vol. 1651. No. 1-2.

Sarray, S. et al. "Lebectin and lebecetin, two C-type lectins from snake venom, inhibit α5β1 and αv-containing integrins" *Matrix Biology*, 2007, pp. 306-313, vol. 26, No. 4.

Written Opinion in International Application No. PCT/EP2017/082482, dated Mar. 9, 2018, pp. 1-12.

Aguilar, E. et al. "Ocular Models of Angiogenesis" *Methods in Enzymology*, 2008, pp. 115-158, vol. 444.

Shao, Z. et al. "Choroid Sprouting Assay: An Ex Vivo Model of Microvascular Angiogenesis" *PLOS ONE*, Jul. 2013, pp. 1-11, vol. 8, Issue 7, e69552.

\* cited by examiner

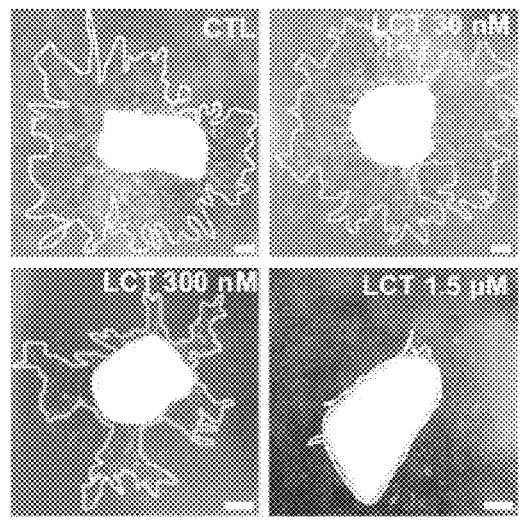 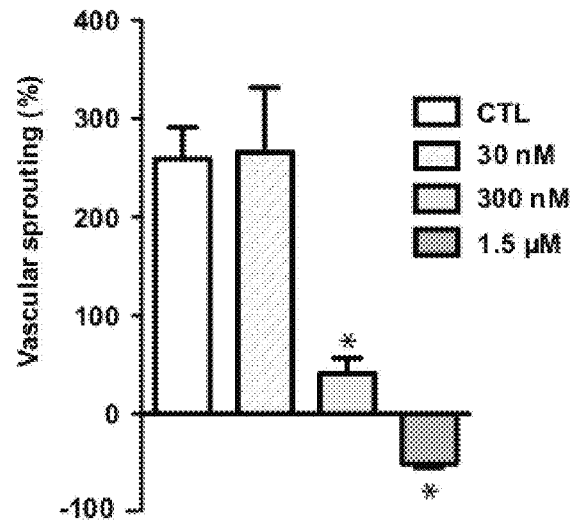
FIG. 1A  FIG. 1B
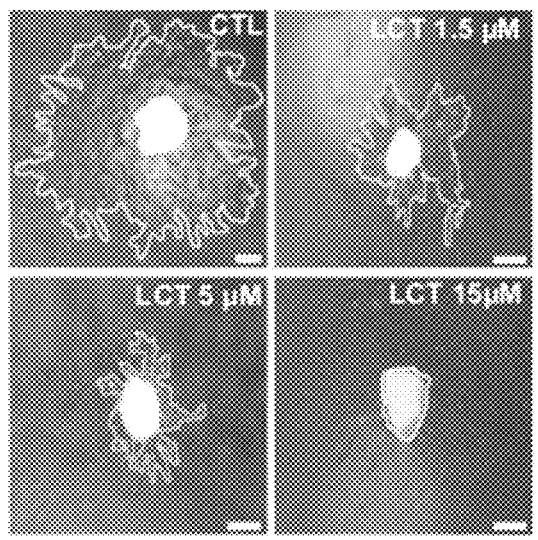 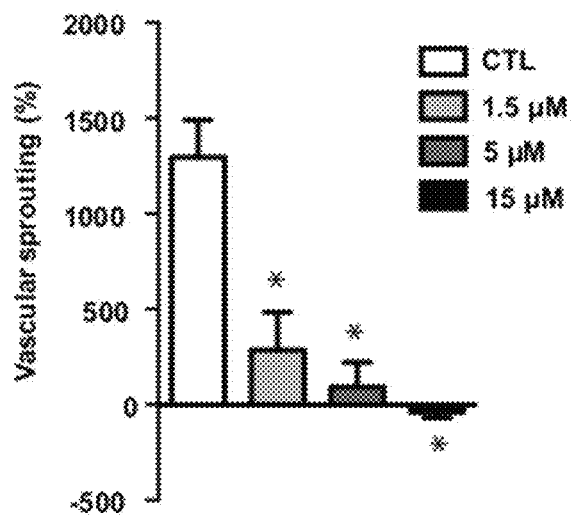
FIG. 1C  FIG. 1D

FIG. 5A
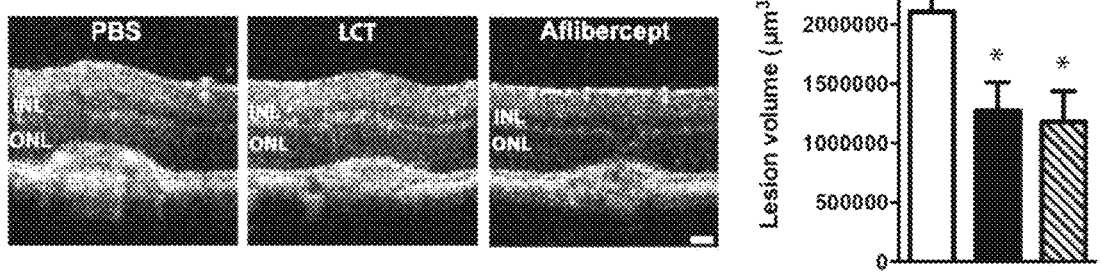
FIG. 5B
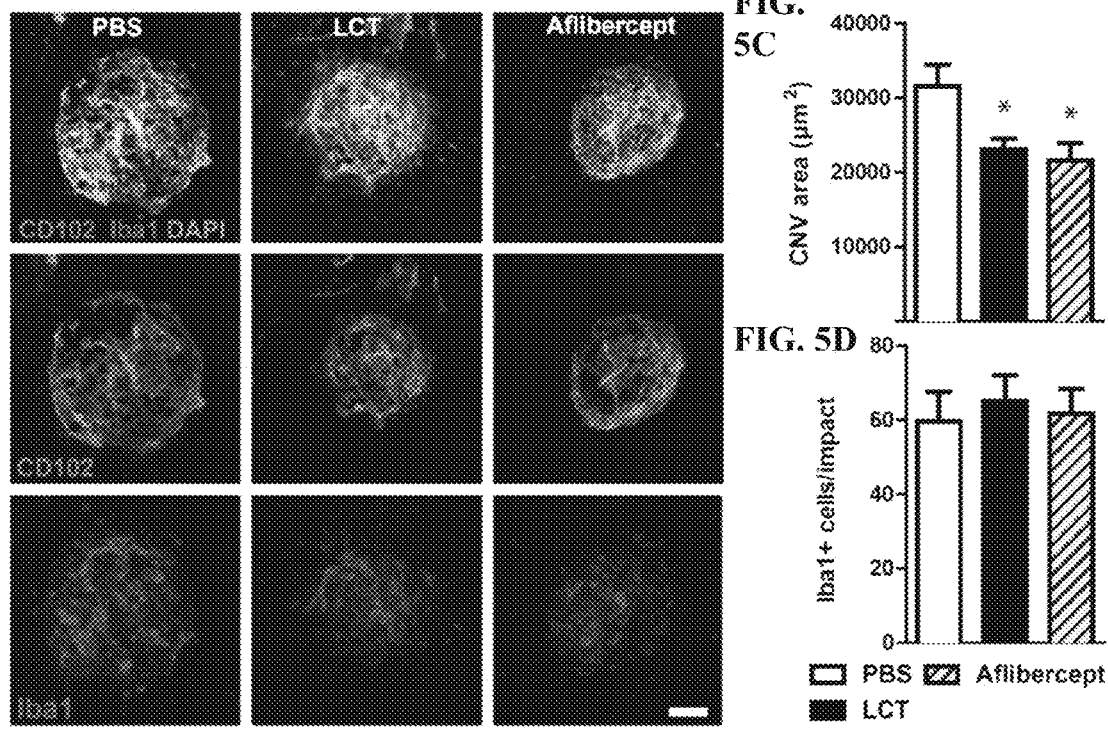
FIG. 5C
FIG. 5D
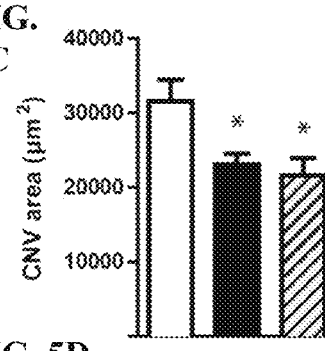
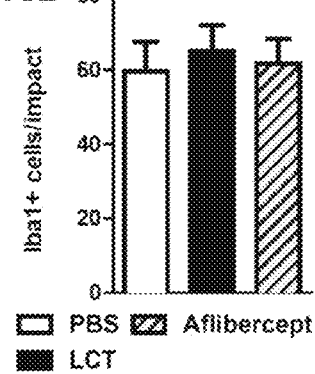
FIG. 5E
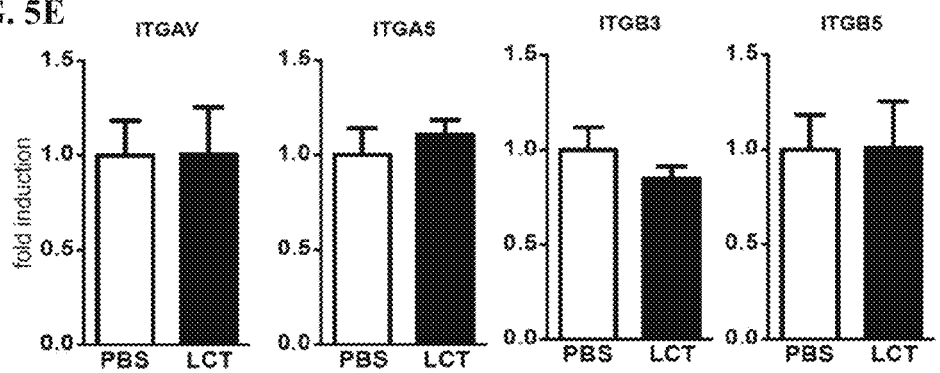

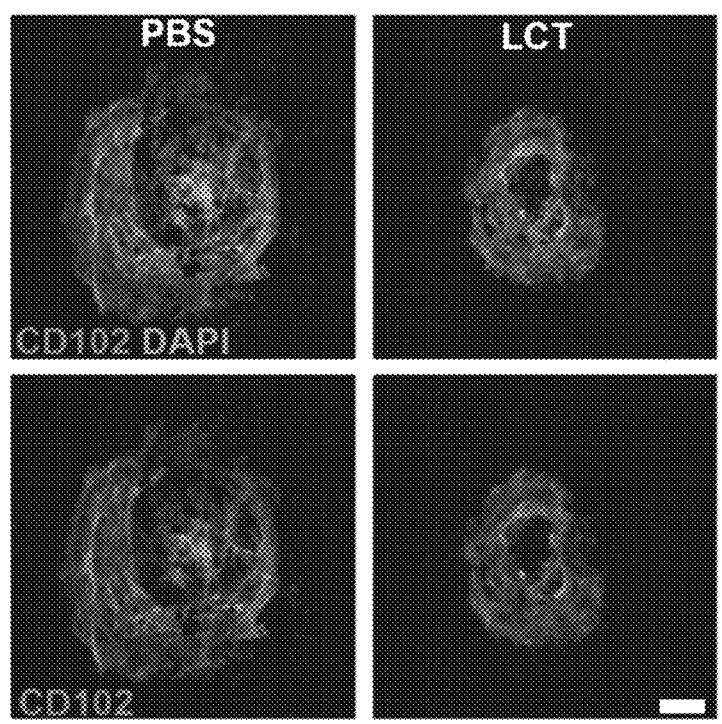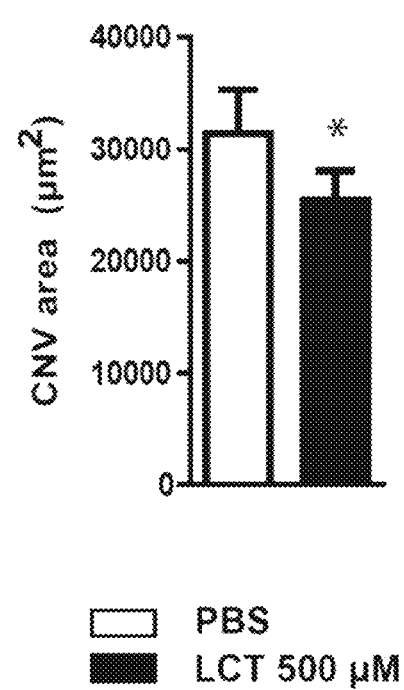
FIG. 6A
FIG. 6B

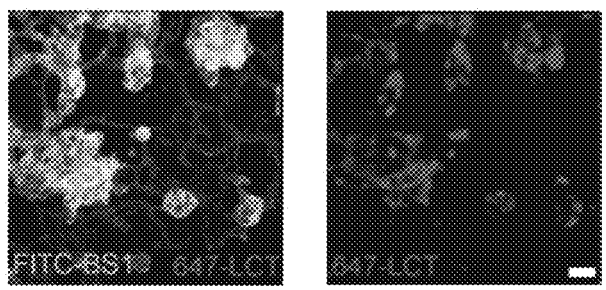
FIG. 7A
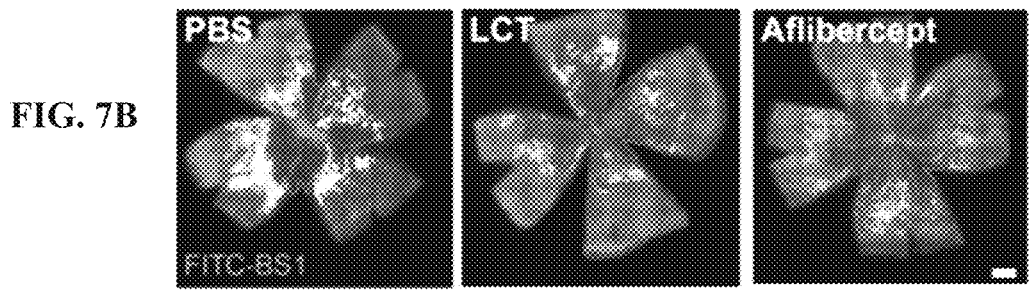
FIG. 7B
FIG. 7C
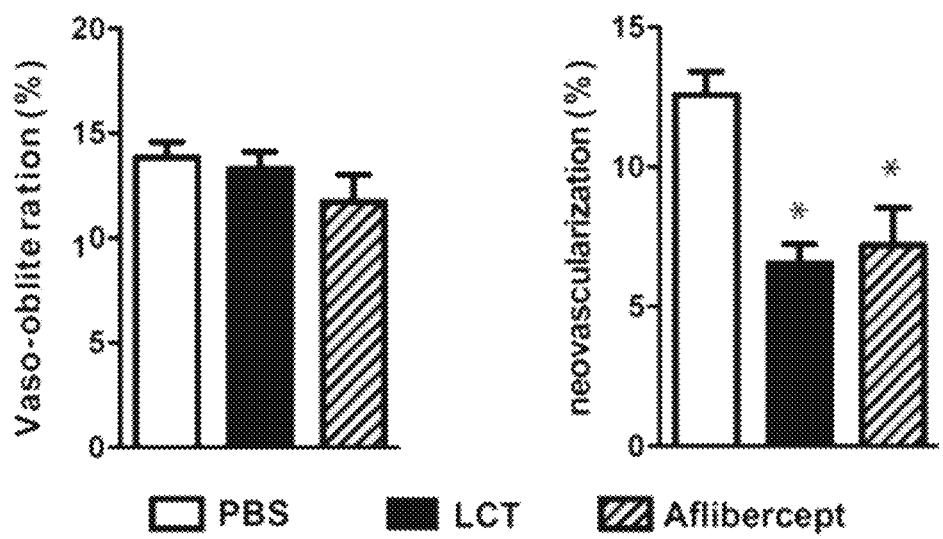
FIG. 7D
FIG. 7E

SEQUENCE LISTING

```
<160> NUMBER OF SEQ ID NOS: 20

<210> SEQ ID NO 1
<211> LENGTH: 156
<212> TYPE: PRT
<213> ORGANISM: Macrovipera lebetina

<400> SEQUENCE: 1

Met Gly Arg Ser Ile Ser Val Ser Phe Gly Leu Leu Val Val Phe Leu
1               5                   10                  15

Ser Leu Ser Gly Thr Gly Ala Asp Gln Asp Cys Leu Pro Gly Trp Ser
            20                  25                  30

Ser His Glu Gly His Cys Tyr Lys Val Phe Asn Leu Asp Lys Thr Trp
        35                  40                  45

Glu Asp Ala Glu Lys Phe Cys Thr Glu Gln Ala Asn Ser Gly His Leu
    50                  55                  60

Val Ser Ile Asp Ser Lys Lys Glu Ala Asn Phe Val Ala Glu Leu Val
65                  70                  75                  80

Ser Gln Asn Ile Lys Glu Thr Arg Arg Thr Asp Phe Val Trp Ile Gly
```

```
                     85                  90                  95

Leu Arg Ala Glu Asp Lys Arg Gln His Cys Ser Ser Glu Trp Ser Asp
            100                 105                 110

Gly Ser Ser Ile Asn Tyr Gln Asn Trp Ile Glu Ala Glu Ser Lys Lys
        115                 120                 125

Cys Leu Gly Leu Glu Lys Gln Thr Arg Tyr Arg Lys Trp Val Asn Leu
    130                 135                 140

Asn Cys Gly Gln Pro Tyr Arg Phe Thr Cys Glu Ile
145                 150                 155

<210> SEQ ID NO 2
<211> LENGTH: 133
<212> TYPE: PRT
<213> ORGANISM: Artificial sequence
<220> FEATURE:
<223> OTHER INFORMATION: Lebecetin alpha subunit without peptide signal
      sequence

<400> SEQUENCE: 2

Asp Gln Asp Cys Leu Pro Gly Trp Ser Ser His Glu Gly His Cys Tyr
1               5                   10                  15

Lys Val Phe Asn Leu Asp Lys Thr Trp Glu Asp Ala Glu Lys Phe Cys
            20                  25                  30

Thr Glu Gln Ala Asn Ser Gly His Leu Val Ser Ile Asp Ser Lys Lys
        35                  40                  45

Glu Ala Asn Phe Val Ala Glu Leu Val Ser Gln Asn Ile Lys Glu Thr
    50                  55                  60

Arg Arg Thr Asp Phe Val Trp Ile Gly Leu Arg Ala Gly Asp Lys Arg
65                  70                  75                  80

Gln His Cys Ser Ser Glu Trp Ser Asp Gly Ser Ser Ile Asn Tyr Gln
                85                  90                  95

Asn Trp Ile Glu Ala Glu Ser Lys Lys Cys Leu Gly Leu Glu Lys Gln
            100                 105                 110

Thr Arg Tyr Arg Lys Trp Val Asn Leu Asn Cys Gly Gln Pro Tyr Arg
        115                 120                 125

Phe Thr Cys Glu Ile
    130

<210> SEQ ID NO 3
<211> LENGTH: 148
<212> TYPE: PRT
<213> ORGANISM: Macrovipera lebetina

<400> SEQUENCE: 3

Met Gly Arg Ile Ile Phe Val Ser Phe Gly Leu Leu Val Val Phe Leu
1               5                   10                  15

Ser Leu Ser Gly Thr Gly Ala Ala Leu Asn Cys Ala Ser Gly Trp Ser
            20                  25                  30

Gly Tyr Asp Gln His Cys Tyr Lys Val Phe Asp Lys Pro Lys Ser Trp
        35                  40                  45

Ala Asp Ala Glu Lys Phe Cys Lys Lys Gln Thr Ser Gly Gly His Leu
    50                  55                  60

Val Ser Phe His Ser Ser Glu Glu Thr Asp Phe Val Val Glu Leu Val
65                  70                  75                  80

Ser Gln Thr Leu Glu Ser Gln Ile Leu Trp Met Gly Leu Ser Lys Val
                85                  90                  95

Trp Asn Gln Cys Asp Trp Gly Trp Ser Asn Gly Ala Lys Leu Lys Tyr
```

```
                    100                 105                 110
Lys Ala Trp Ala Glu Glu Ser Tyr Cys Val Tyr Phe Ser Ser Thr Lys
            115                 120                 125

Lys Gly Trp Arg Ser Arg Ala Cys Arg Leu Leu Gly His Phe Val Cys
        130                 135                 140

Lys Ser Pro Ala
145

<210> SEQ ID NO 4
<211> LENGTH: 114
<212> TYPE: PRT
<213> ORGANISM: Artificial sequence
<220> FEATURE:
<223> OTHER INFORMATION: Lebecetin beta subunit without peptide signal
      sequence

<400> SEQUENCE: 4

Asp Gln His Cys Tyr Lys Val Phe Asp Lys Pro Lys Ser Trp Ala Asp
1               5                   10                  15

Ala Glu Lys Phe Cys Lys Lys Gln Thr Ser Gly Gly His Leu Val Ser
            20                  25                  30

Phe His Ser Ser Glu Glu Thr Asp Phe Val Val Glu Leu Val Ser Gln
        35                  40                  45

Thr Leu Glu Ser Gln Ile Leu Trp Met Gly Leu Ser Lys Val Trp Asn
    50                  55                  60

Gln Cys Asp Trp Gly Trp Ser Asn Gly Ala Lys Leu Lys Tyr Lys Ala
65                  70                  75                  80

Trp Ala Glu Glu Ser Tyr Cys Val Tyr Phe Ser Ser Thr Lys Lys Gly
                85                  90                  95

Trp Arg Ser Arg Ala Cys Arg Leu Leu Gly His Phe Val Cys Lys Ser
            100                 105                 110

Pro Ala

<210> SEQ ID NO 5
<211> LENGTH: 21
<212> TYPE: DNA
<213> ORGANISM: Artificial sequence
<220> FEATURE:
<223> OTHER INFORMATION: Sense primer for GAPDH amplification

<400> SEQUENCE: 5
acggccgcat cttcttgtgc a                                          21

<210> SEQ ID NO 6
<211> LENGTH: 20
<212> TYPE: DNA
<213> ORGANISM: Artificial sequence
<220> FEATURE:
<223> OTHER INFORMATION: Antisense primer for GAPDH amplification

<400> SEQUENCE: 6
caggcgccca atacggccaa                                            20

<210> SEQ ID NO 7
<211> LENGTH: 20
<212> TYPE: DNA
<213> ORGANISM: Artificial sequence
<220> FEATURE:
<223> OTHER INFORMATION: Sense primer for ITGAV amplification

<400> SEQUENCE: 7
``` cacccctcaga gagggagatg                                              20

<210> SEQ ID NO 8
<211> LENGTH: 20
<212> TYPE: DNA
<213> ORGANISM: Artificial sequence
<220> FEATURE:
<223> OTHER INFORMATION: Antisense primer for ITGAV amplification

<400> SEQUENCE: 8
acgtacagga ttgcgctctt                                               20

<210> SEQ ID NO 9
<211> LENGTH: 20
<212> TYPE: DNA
<213> ORGANISM: Artificial sequence
<220> FEATURE:
<223> OTHER INFORMATION: Sense primer for ITGA5 amplification

<400> SEQUENCE: 9
agtacgcacc ttgccgctca                                               20

<210> SEQ ID NO 10
<211> LENGTH: 21
<212> TYPE: DNA
<213> ORGANISM: Artificial sequence
<220> FEATURE:
<223> OTHER INFORMATION: Antisense primer for ITGA5 amplification

<400> SEQUENCE: 10
acacggccag tcttggtgaa c                                             21

<210> SEQ ID NO 11
<211> LENGTH: 20
<212> TYPE: DNA
<213> ORGANISM: Artificial sequence
<220> FEATURE:
<223> OTHER INFORMATION: Sense primer for ITGB3 amplification

<400> SEQUENCE: 11
aaccggggaa cgctccatga                                               20

<210> SEQ ID NO 12
<211> LENGTH: 21
<212> TYPE: DNA
<213> ORGANISM: Artificial sequence
<220> FEATURE:
<223> OTHER INFORMATION: Antisense primer for ITGB3 amplification

<400> SEQUENCE: 12
cggcgttttt gccagtatcc g                                             21

<210> SEQ ID NO 13
<211> LENGTH: 21
<212> TYPE: DNA
<213> ORGANISM: Artificial sequence
<220> FEATURE:
<223> OTHER INFORMATION: Sense primer for ITGB5 amplification

<400> SEQUENCE: 13
agcctttggg gagacgtgtg a                                             21

<210> SEQ ID NO 14
<211> LENGTH: 20
<212> TYPE: DNA
<213> ORGANISM: Artificial sequence
<220> FEATURE:
<223> OTHER INFORMATION: Antisense primer for ITGB5 amplification

<400> SEQUENCE: 14
tggtggtggc aggtctggtt    20

<210> SEQ ID NO 15
<211> LENGTH: 154
<212> TYPE: PRT
<213> ORGANISM: Artificial Sequence
<220> FEATURE:
<223> OTHER INFORMATION: Lebecetin alpha subunit with peptide signal
      sequence

<400> SEQUENCE: 15

Met Ala Cys Pro Gly Phe Leu Trp Ala Leu Val Ile Ser Thr Cys Leu
1               5                   10                  15

Glu Phe Ser Met Ala Asp Gln Asp Cys Leu Pro Gly Trp Ser Ser His
            20                  25                  30

Glu Gly His Cys Tyr Lys Val Phe Asn Leu Asp Lys Thr Trp Glu Asp
        35                  40                  45

Ala Glu Lys Phe Cys Thr Glu Gln Ala Asn Ser Gly His Leu Val Ser
    50                  55                  60

Ile Asp Ser Lys Lys Glu Ala Asn Phe Val Ala Glu Leu Val Ser Gln
65                  70                  75                  80

Asn Ile Lys Glu Thr Arg Arg Thr Asp Phe Val Trp Ile Gly Leu Arg
                85                  90                  95

Ala Glu Asp Lys Arg Gln His Cys Ser Ser Glu Trp Ser Asp Gly Ser
            100                 105                 110

Ser Ile Asn Tyr Gln Asn Trp Ile Glu Ala Glu Ser Lys Lys Cys Leu
        115                 120                 125

Gly Leu Glu Lys Gln Thr Arg Tyr Arg Lys Trp Val Asn Leu Asn Cys
    130                 135                 140

Gly Gln Pro Tyr Arg Phe Thr Cys Glu Ile
145                 150

<210> SEQ ID NO 16
<211> LENGTH: 146
<212> TYPE: PRT
<213> ORGANISM: Artificial Sequence
<220> FEATURE:
<223> OTHER INFORMATION: Lebecetin beta subunit with peptide signal
      sequence

<400> SEQUENCE: 16

Met Ala Cys Pro Gly Phe Leu Trp Ala Leu Val Ile Ser Thr Cys Leu
1               5                   10                  15

Glu Phe Ser Met Ala Ala Leu Asn Cys Ala Ser Gly Trp Ser Gly Tyr
            20                  25                  30

Asp Gln His Cys Tyr Lys Val Phe Asp Lys Pro Lys Ser Trp Ala Asp
        35                  40                  45

Ala Glu Lys Phe Cys Lys Lys Gln Thr Ser Gly Gly His Leu Val Ser
    50                  55                  60

Phe His Ser Ser Glu Glu Thr Asp Phe Val Val Lys Leu Val Ser Gln
65                  70                  75                  80

Thr Leu Glu Ser Gln Ile Leu Trp Met Gly Leu Ser Lys Val Trp Asn
                85                  90                  95

Gln Cys Asp Trp Gly Trp Ser Asn Gly Ala Lys Leu Lys Tyr Lys Ala
            100                 105                 110

```
Trp Ala Glu Glu Ser Tyr Cys Val Tyr Phe Ser Ser Thr Lys Lys Gly
        115                 120                 125

Trp Arg Ser Arg Ala Cys Arg Leu Leu Gly His Phe Val Cys Lys Ser
        130                 135                 140

Pro Ala
145

<210> SEQ ID NO 17
<211> LENGTH: 21
<212> TYPE: PRT
<213> ORGANISM: Artificial Sequence
<220> FEATURE:
<223> OTHER INFORMATION: Peptide signal sequence

<400> SEQUENCE: 17

Met Ala Cys Pro Gly Phe Leu Trp Ala Leu Val Ile Ser Thr Cys Leu
1               5                   10                  15

Glu Phe Ser Met Ala
            20

<210> SEQ ID NO 18
<211> LENGTH: 125
<212> TYPE: PRT
<213> ORGANISM: Artificial Sequence
<220> FEATURE:
<223> OTHER INFORMATION: Lebecetin beta subunit without  peptide signal
      sequence

<400> SEQUENCE: 18

Ala Leu Asn Cys Ala Ser Gly Trp Ser Gly Tyr Asp Gln His Cys Tyr
1               5                   10                  15

Lys Val Phe Asp Lys Pro Lys Ser Trp Ala Asp Ala Glu Lys Phe Cys
            20                  25                  30

Lys Lys Gln Thr Ser Gly Gly His Leu Val Ser Phe His Ser Ser Glu
        35                  40                  45

Glu Thr Asp Phe Val Val Lys Leu Val Ser Gln Thr Leu Glu Ser Gln
    50                  55                  60

Ile Leu Trp Met Gly Leu Ser Lys Val Trp Asn Gln Cys Asp Trp Gly
65                  70                  75                  80

Trp Ser Asn Gly Ala Lys Leu Lys Tyr Lys Ala Trp Ala Glu Glu Ser
                85                  90                  95

Tyr Cys Val Tyr Phe Ser Ser Thr Lys Lys Gly Trp Arg Ser Arg Ala
            100                 105                 110

Cys Arg Leu Leu Gly His Phe Val Cys Lys Ser Pro Ala
        115                 120                 125

<210> SEQ ID NO 19
<211> LENGTH: 4
<212> TYPE: PRT
<213> ORGANISM: Artificial sequence
<220> FEATURE:
<223> OTHER INFORMATION: lebecetin domain

<400> SEQUENCE: 19

Asp Ala Glu Lys
1

<210> SEQ ID NO 20
<211> LENGTH: 4
<212> TYPE: PRT
<213> ORGANISM: Artificial sequence
```

```
<220> FEATURE:
<223> OTHER INFORMATION: lebecetin motif

<400> SEQUENCE: 20

Trp Ile Gly Leu
1
```

LEBECETIN, A C-TYPE LECTIN, AS NEOVASCULARIZATION INHIBITOR

CROSS-REFERENCE TO RELATED APPLICATION

This application is the U.S. national stage application of International Patent Application No. PCT/EP2017/082482, filed Dec. 12, 2017.

The Sequence Listing for this application is labeled "Seq-List-replace-2.txt" which was created on May 19, 2021 and is 12 KB. The entire content of the sequence listing is incorporated herein by reference in its entirety.

FIELD OF THE INVENTION

The present invention relates to the field of medicine, in particular to the treatment of diseases involving neovascularization, and preferably to the treatment of ocular diseases involving retinal neovascularization.

BACKGROUND OF THE INVENTION

Age related Macular degeneration (AMD) is the leading cause of blindness in people over 55 years of age, and ischemic retinopathies such as diabetic retinopathy (DR), retinal vein occlusion and retinopathy of prematurity, is the leading cause of blindness in people under 55 years of age (Friedman D S et al. 2004; Kempen J H et al. 2004; Klein Ret al. 2004). Proliferative forms of these pathologies (wet AMD and proliferative diabetic retinopathy) result in rapid and non-reversible vision loss. In AMD, new vessels mainly originate from the vascular choroidal bed and grow in the subretinal space or underneath the retinal pigment epithelium (RPE) while in the proliferative form of DR (PDR), neural ischemia trigger neovascularization from the retinal vessels.

Neoangiogenesis, also called neovascularization, is a fundamental process of capillary sprouting and configuring of neovasculatures from the existing blood vessels. It is in contrast to vasculogenesis/angiogenesis, another process of blood vessel formation occurring during embryologic development of the circulatory system or in the adult organism from circulating endothelial progenitor cells.

Vascular endothelial growth factor (VEGF) is a major mediator of retinal and choroidal angiogenesis (D'Amore P. A. et al. 1994). Intraocular injections of antibodies directed against VEGF or of soluble form of VEGFR1 efficiently inhibit choroidal neovascularization in wet AMD. However 10% of the treatment-naïve patients do not respond to anti-VEGF (Brown, D. M. et al. 2006; Rosenfeld P. J. et al. 2006) and 2 to 10% of the anti-VEGF responders become resistant with time (Forooghian, F. et al. 2009; Eghøj, M. S. et al. 2012). Anti-VEGF therapies are also the first line treatment of diabetic macular edema. In contrast, PDR that are characterized by retinal neovascularization (RNV) are mostly treated by a preventive pan-retinal photocoagulation (PRP) (Martinez-Zapata, M. J. et al. 2014). Anti-VEGFs are now approved in the US for the treatment of PDR as an alternative to PRP. Ongoing studies will determine the rate of spontaneous and acquired resistance in this new indication. All together, these clinical data support the need for additional anti-neovascularization therapies that do not primarily target the VEGF pathway.

Furthermore, because retinal neovascularization is associated with exudation and hemorrhages that are responsible for rapid loss of vision, the identification of alternative pathways to block excessive neoangiogenesis and vascular leakage is thus of enormous therapeutic interest.

SUMMARY OF THE INVENTION

The inventors herein revealed an unanticipated effect of lebecetin. Indeed, they demonstrated that lebecetin can efficiently reduce the extent of choroidal or retinal neovascularization and thus provide new strategies to inhibit neovascularization.

Accordingly, in a first aspect the present invention relates to a protein selected from lebecetin and functional variants and fragments thereof for use in the treatment of neovascular disease.

In particular, this protein may be lebecetin or may be a functional variant of lebecetin comprising a first subunit comprising, or consisting of, the amino acid sequence SEQ ID NO: 1 or SEQ ID NO: 2, or an amino sequence having at least 75% identity with SEQ ID NO: 1 or SEQ ID NO: 2 and a second subunit comprising, or consisting of, the amino sequence SEQ ID NO: 3 or SEQ ID NO: 4, or an amino sequence having at least 75% identity with SEQ ID NO: 3 or SEQ ID NO: 4. Said functional variant of lebecetin can also comprise a first subunit comprising, or consisting of, a sequence derived from SEQ ID NO: 1 or 2 and comprising from 1 to 30 amino acid conservative substitutions, and/or a second subunit comprising, or consisting of, a sequence derived from SEQ ID NO: 3 or 4 and comprising from 1 to 30 amino acid conservative substitutions. Preferably, residues corresponding to 1) cysteine residues involved in intra or inter disulfide bridges between alpha and beta chains, i.e. Cys27, Cys38, Cys55, Cys106, Cys129, Cys149 and Cys 154 of SEQ ID NO: 1, and Cys27, Cys38, Cys55, Cys100, Cys123, Cys136 and Cys 144 of SEQ ID NO: 3; and/or 2) residues of HCY domains, i.e. His37, Cys38, Tyr39 of SEQ ID NO: 1 and His37, Cys38, Tyr39 of SEQ ID NO: 3; and/or 3) residues of DAEK (SEQ ID NO: 19) domains, i.e. Asp50, Ala51, Glu52 and lys53 of SEQ ID NO: 1 and Asp50, Ala51, Glu52 and lys53 of SEQ ID NO: 3; and/or 4) residues of WIGL (SEQ ID NO: 20) motifs, i.e. Trp94 to Leu96 of SEQ ID NO: 1 and Trp94 to Leu96 of SEQ ID NO: 3, are conserved in the functional variant of lebecetin.

Preferably, the protein used according to the invention is isolated from *M. lebetina* venom or is a recombinant protein.

In a second aspect, the present invention relates to a nucleic acid sequence encoding the protein used according to the invention, or an expression vector comprising said nucleic acid, for use in the treatment of neovascular disease.

In a third aspect, the present invention relates to a pharmaceutical composition comprising the protein, the nucleic acid or the vector used according to the present invention and a pharmaceutical excipient. The present invention also relates to said pharmaceutical composition for use in the treatment of neovascular disease. Preferably said pharmaceutical composition further comprises at least one additional active substance, preferably one angiogenesis inhibitor, more preferably an inhibitor of the VEGF pathway.

In particular embodiments, said pharmaceutical composition can be used in combination with at least one angiogenesis inhibitor, preferably an inhibitor of the VEGF pathway.

Preferably, the subject to be treated with the pharmaceutical composition of the invention is a subject who does not respond or became resistant to a therapy with angiogenesis inhibitor, preferably an inhibitor of the VEGF pathway.

The neovascular disease may be selected from the group consisting of ocular neovascular diseases and cancers with a neovascular component. In some embodiments, the neovascular disease is an ocular neovascular disease, preferably selected from the group consisting of age-related macular degeneration, diabetic retinopathies such as diabetic retinal ischemia or proliferative diabetic retinopathy, iris neovascularization, intraocular neovascularization, corneal neovascularization, retinal neovascularization, choroidal neovascularization and corneal inflammation. In some other embodiments, the neovascular disease is a cancer with a neovascular component, preferably selected from the group consisting of lung, breast, gastric, colorectal, pancreas and brain cancer.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1A-1D: LCT inhibits vascular sprouting from aortic and choroidal explants. (FIGS. 1A, 1C) Representative microphotographs of aortic and choroidal endothelial sprouts. (FIGS. 1B) Measurement of vascular sprouting from aortic rings from P4 Lewis rat pups in control and LCT (30 nM, 300 nM, 1.5 µM) groups, (n=4 per group, *p 0.05; one-way ANOVA followed by Dunnett's post-test; CTL as control, representative of 3 independent experiments). (FIG. 1D) Measurement of vascular sprouting from choroidal explants from 3-weeks-old C57BL/6JRj male mice in control and LCT (1.5 µM, 5 µM, 15 µM) groups, (n≥5 per group, *p<0.05; one-way ANOVA followed by Dunnett's post-test; CTL as control, representative of 3 independent experiments). Scale bars in A and C=200 µm.

(FIG. 2A) Representative SD-OCT image of retina at D7 post-intravitreal injection of 1 µl of PBS or LCT (500 µM). (FIG. 2B) Quantification of the thickness of the entire retina, ONL, INL and OS at 500 µm of the optic nerve, n=4 eyes per group. (FIG. 2C) Representative electroretinogram traces from scotopic ERG recording of CTL, PBS and LCT groups at 0.3 cds/m². (FIG. 2D) Scotopic recorded a- and b-waves amplitudes at different stimulus intensities (0.003 cd.s/m²; 0.03 cd.s/m²; 0.3 cd.s/m²; 3 cd.s/m²; 10 cd.s/m²). (FIG. 2E) Photopic response amplitudes at flash intensity of 10 cd.s/m² of light adapted animals. (FIG. 2F) Representative electroretinogram traces from ERG flickers recorded at flash frequencies of 10 Hz at 1 cd.s/m² intensity. (FIG. 2G) Flicker response amplitudes recorded at flash frequencies of 10 and 20 Hz, n=10 eyes per group for each ERG recording. IPL: Inner plexiform layer, INL: Inner nuclear layer, ONL: Outer nuclear layer, OLM: Outer limiting membrane. Scale bar in A=100 µm.

(FIG. 3A) Microphotographs of retinal flatmounts from C57BL/6JRj mice immunostained with FITC-coupled BS-1 lectin (green), collagen-IV (red), and (FIG. 3B) GFAP (green) 7 days after intravitreal injections of PBS (1 µl) or LCT (1 µl, 500 µM). (FIG. 3C) Microphotographs of retinal flatmounts from CX3CR1$^{+/GFP}$ mice immunostained with collagen-IV (red) and Iba1 (green) antibodies in the inner and outer plexus 7 days after intravitreal injections of PBS (1 µl) or LCT (1 µl, 500 µM). (FIG. 3D) Choroidal flatmounts from C57BL/6JRj mice co-immunostained with TRITC-coupled phalloidin (red) and DAPI (blue) at D7 after intravitreal injections of PBS (1 µl) or LCT (1 µl, 500 µM). Scale bars in A, B and C=50 µm; in D=100 µm.

FIG. 5A-5E: LCT inhibits laser-induced choroidal neovascularization. (FIG. 5A) Representative SD-OCT images of choroidal lesion and quantification of lesion volume 7 days after laser and intravitreal injections of PBS (1 µl), LCT (1 µl, 500 µM) and Aflibercept (1 µl, 25 µM). (n=26, 35 and 16 respectively laser impacts per group. *p<0.05; one-way ANOVA followed by Bonferroni post-test; representative of 2 independent experiments) Lesion volume is extrapolated using following formula $(4/3\pi*a*b^2)/2$, a is the polar radius (vertical axis) and b is the equator radius (horizontal axis). (FIG. 5B) Microphotographs of CNV lesion on choroidal flatmounts of PBS (1 µl), LCT (1 µl, 500 µM) and Aflibercept (1 µl, 25 µM) stained with CD102 (green), Iba1 (red) and DAPI (blue). (FIG. 5C) Quantification of CNV (CD102-positive area) 7 days after laser and intravitreal injections of PBS (1 µl), LCT (1 µl, 500 µM) and Aflibercept (1 µl, 25 µM) (n=29, 32 and 30 respectively laser impacts per group. *p<0.05; one-way ANOVA followed by Bonferroni post-test; representative of 2 independent experiments). (FIG. 5D) Quantification of Iba1 positive cells per impact 7 days after laser and intravitreal injections of PBS (1 µl), LCT (1 µl, 500 µM) and Aflibercept (1 µl, 25 µM) (n=29, 32 and 30 respectively laser impacts per group. *p<0.05; one-way ANOVA followed by Bonferroni post-test; representative of 2 independent experiments). (FIG. 5E) Quantitative RT-PCR of integrin subunit mRNA (αv, α5, β3, β5) normalized with GADPH mRNA of C57BL/6JRj choroids at D3. Mice were treated with a single intravitreal injection of PBS (1 µl) or LCT (1 µl, 500 µM) at D2, n=5 eyes per group. INL: inner nuclear layer, ONL: outer nuclear layer, Scale bars in A=50 µm; in B=100 µm.

FIGS. 6A-6B: LCT intravitreal injection at D3 inhibits choroidal neovascularization. (FIG. 6A) Microphotographs of CNV lesions stained with CD102 (green), and DAPI (blue) 7 days after laser (D0) and intravitreal injections (D3) of PBS (1 µl), LCT (1 µl, 500 µM). (FIG. 6B) Quantification of CNV (CD102-positive area) on PBS and LCT choroidal flatmounts at D7 (n=27 and 28 laser impacts per group. *p<0.05; Mann-Whitney U test; representative of 2 independent experiments), Scale bar in A=100 µm.

FIGS. 7A-7E: LCT inhibits retinal neovascularization in the Oxygen Induced Retinopathy (OIR) model. (FIG. 7A) Microphotographs of FITC-coupled BS-1 lectin-stained retina (green) of P17-OIR C57BL/6JRj mice that received an intravitreal injection at P14 of LCT (647-LCT) covalently conjugated to an Alexa Fluor 647 dye (red). (FIG. 7B) Microphotographs of FITC-coupled BS-1 lectin-stained retina, of P17-OIR C57BL/6JRj mice, after intravitreal injection at P12 of PBS (1 µl), LCT (1 µl, 500 µM) or Aflibercept (1 µl, 25 µM). Neovascularization (NV) and vaso-obliteration (VO) areas were highlighted in white and red respectively. (FIG. 7C) Representative confocal microscopy photographs of neovascularization in BS-1 lectin-stained control and treated retinas. (FIG. 7D) Quantification of vaso-obliteration and (FIG. 7E) neovascularization (BS-1 lectin positive-area) in P17 control and treated retinal flatmounts, (n=35, 32 and 16 OIR-retina respectively. *p<0.05; one-way ANOVA followed by Bonferroni post-test; representative of 2 independent experiments). Scale bars in A=30 µm; in B=80 mm; and in C=100 µm.

(FIG. 8A) Quantification of neovascularization (BS-1 lectin positive-area) and (B) Vaso-obliteration in P17-OIR C57BL/6JRj mice, after intravitreal injection at P12 of PBS (1 µl), LCT (1 82 1, 500 µM), Aflibercept (1 µl, 25 µM) or LCT+Aflibercept (1 µl 500 µM LCT/25 µM Aflibercept), (n=35, 32, 16 and 24 OIR-retina respectively) .*p<0.05; one-way ANOVA followed by dunnett's post-test; representative of 2 independent experiments).

(FIG. 9A) Representative microphotographs of untreated (CTL) choroidal endothelial sprouts or choroidal endothelial sprouts at day 6 (D6) treated with Lebecetin from *Macrovipera lebetina* (LCT) or recombinant LCT (rLCT) at D3. (FIG. 9B) Measurement of vascular sprouting of choroidal explants from 2-weeks-old C57BL/6JRj male mice in control, LCT (1.5 µM) and rLCT (1.5 µM, 5 µM, 15 µM) groups. Vascular sprouting is expressed as the increased between D3 and D6. (n≥10 per group, *p<0.05; one-way ANOVA followed by Dunnett's post-test; CTL as control. (FIG. 9C) Measurement of vascular sprouting of choroidal explants from 2-weeks-old C57BL/6JRj male mice treated for 3 days with 2.5 µM Aflibercept, in control, LCT (1.5 µM) and rLCT (1.5 µM, 5 µM, 15 µM) groups, (n≥6 per group, *p<0.05; one-way ANOVA followed by Dunnett's post-test; Afli as control). Scale bar in A 500 µm.

(FIG. 10A) Microphotographs of CD102-stained retina, of P17-OIR C57BL/6JRj mice, injected intravitreally at P12 with PBS (1 µl) or recombinant LCT (rLCT, 1 µl, 500 µM). Quantification of (FIG. 10B) vaso-obliteration and (FIG. 10C) neovascularization (CD102 positive-area) in P17 control and treated retinal flatmounts, (n=9 and 10 OIR-retina respectively. *p<0.05; unpaired t-test). Scale Bar in A=500 µm; inset=40 µm.

(FIG. 11A) Microphotographs of CNV lesion on choroidal flatmounts of PBS and recombinant LCT (rLCT) stained with CD102. (FIG. 11B) Quantification of CNV (CD102-positive area) 7 days after laser and intravitreal injections of PBS (1 µl) and rLCT (1 µl, 500 µM) (n=29, 32 and 30 respectively laser impacts per group. *p<0.05; one-way ANOVA followed by Bonferroni post-test; representative of 2 independent experiments). (E) Quantification of Iba1 positive cells per impact 7 days after laser and intravitreal injections of PBS (1 µl), LCT (1 µl, 500 µM) and Aflibercept (1 µl, 1.7 µg) (n=35 and 47 respectively laser impacts per group. *p<0.05; unpaired t-test). Scale bar in A=50 µm.

DETAILED DESCRIPTION OF THE INVENTION

Figure 2A:
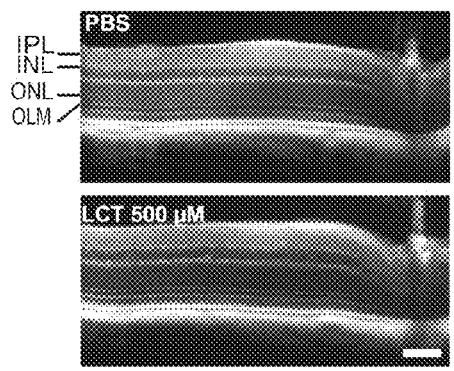
FIGS. 2A-2G: LCT intravitreal injection does not alter visual function.

The inventors herein demonstrated that lebecetin was effective at reducing vascular sprouting in ex vivo models of neovascularization, i.e. aortic and choroidal explants, as well as in vivo models of neovascularization, i.e. laser induced choroidal neovascularization and oxygen induced retinopathy model, with an efficiency comparable to anti-VEGF therapy. Indeed, they observed that intravitreal injection of lebecetin allowed prevention and regression of neovascularization. They also showed that intravitreal injection of therapeutically efficient amount of lebecetin does not alter retinal architecture, retinal function or vessel integrity.

These results thus clearly demonstrate that lebecetin can be efficiently used to treat diseases involving neovascularization, and in particular retinal and/or choroidal neovascularization.

Thus, in a first aspect, the present invention relates to a protein selected from lebecetin, and functional variants and fragments thereof, for use in the treatment of a neovascular disease.

As used herein, the term "Lebecetin" or "LCT" refers to a C-type lectin (CTL) of 30 kDa isolated from *Macrovipera lebetina* (MVL). CTLs share common features including a cysteine scaffold (with a minimum of 4 cysteine) and a Carbohydrate Recognition Domain (CRD) or CRD-like. LCT is composed of an alpha chain (MLVA1) (SEQ ID NO: 1) and a beta chain (MLVB1) (SEQ ID NO: 3). Both subunits have been cloned (Jebali et al. 2009) and are indexed in Genbank database (Accession Numbers: ABW82656 and ABW82672, respectively). The two subunits are linked by disulfide links (Sarray, S. et al. 2003). MLVA1 and MLVB1 have a CLECT domain, i.e. a carbohydrate-recognition domain (MVLA1, residue 27 to 155 domain (cdd 295302) and MVLB1 residue 27 to 145 domain (cdd 214480)). Homodimeric forms of MLVA1 or MLVB1 are not active (Jebali et al. 2012). The putative lebecetin "signal peptide" sequences from the start codon to codon 24 can be omitted.

As used herein, the term "functional fragment" refers to a heterodimer protein which is derived from lebecetin, retains the anti-neovascularization activity of lebecetin, and comprises i) the alpha chain of lebecetin (SEQ ID NO: 1) and a fragment of the beta chain of lebecetin, ii) a fragment of the alpha chain of lebecetin and the beta chain of lebecetin (SEQ ID NO: 3), or (iii) a fragment of the alpha chain of lebecetin and a fragment of the beta chain of lebecetin.

Preferably, the fragment of the alpha chain comprises, or consists of, an amino acid sequence comprising at least 100, 110 or 120, more preferably at least 130 contiguous amino acids of SEQ ID NO: 1, and/or the fragment of the beta chain comprises, or consists of, an amino acid sequence comprising at least 100 or 110, more preferably at least 120 contiguous amino acids of SEQ ID NO: 3. Preferably said contiguous amino acids include the C-terminal ends of the subunits.

Preferably, the term "functional fragment" refers to a mature form of lebecetin i.e. that does not contain a signal peptide at the N-terminal end of one or both of the subunits, preferably of both of the subunits. Thus, in a particular embodiment, the protein used in the present invention is a functional fragment of lebecetin which is a heterodimer made of two different subunits: a first subunit comprising, or consisting of, SEQ ID NO: 2, and a second subunit comprising, or consisting of SEQ ID NO: 4, these two subunits being linked by disulfide bridges.

In an embodiment, the protein used in the present invention is a heterodimer made of two different subunits: a first subunit comprising, or consisting of, SEQ ID NO: 1 or 2, and a second subunit comprising, or consisting of SEQ ID NO: 3 or 4, these two subunits being linked by disulfide bridges.

In a particular embodiment, the protein used in the present invention comprises a first subunit comprising, or consisting of, SEQ ID NO: 1 and a second subunit comprising, or consisting of, SEQ ID NO: 3.

In another particular embodiment, the protein used in the present invention comprises a first subunit comprising, or consisting of, SEQ ID NO: 2 and a second subunit comprising, or consisting of, SEQ ID NO: 4.

In another particular embodiment, the protein used in the present invention is a heterodimer comprising two different subunits : a first subunit comprising, or consisting of, SEQ ID NO: 2 and a second subunit comprising, or consisting of, SEQ ID NO: 4 or 18, these two subunits being linked by disulfide bridges.

As used herein, the term "functional variant" refers to a heterodimer protein which is derived from lebecetin and comprises an alteration, i.e., a substitution, insertion, and/or deletion, at one or more (e.g., several) positions in one or both of its subunits, and retains the anti-neovascularization activity of lebecetin. This activity may be easily assessed as described in the experimental section below. The term "deletion", used in relation to a position or an amino acid, means that the amino acid in the particular position has been deleted or is absent. The term "insertion", used in relation to a position or amino acid, means that one or more amino acids have been inserted or are present adjacent to and immediately following the amino acid occupying the particular position. The term "substitution", as used herein in relation to a position or amino acid, means that the amino acid in the particular position has been replaced by another amino acid or that an amino acid different from the one of the wild-type protein is present. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, aminobutyric acid, ornithine), and non-naturally occurring amino acid, often made synthetically, (e.g. norleucine, norvaline and cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The variant may be obtained by various techniques well known in the art. In particular, examples of techniques for altering the DNA sequence encoding the wild-type protein, include, but are not limited to, site-directed mutagenesis, random mutagenesis and synthetic oligonucleotide construction.

More particularly, the term "functional variant" refers to an heterodimer made of two different subunits: a first subunit comprising, or consisting of, a sequence having at least 75% identity to SEQ ID NO: 1 or 2, and a second subunit comprising, or consisting of, a sequence having at least 75% identity to SEQ ID NO: 3 or 4, said variant retaining the anti-neovascularization activity of lebecetin.

In an embodiment, the functional variant comprises a first subunit comprising, or consisting of, a sequence having at least 75%, 80%, 85%, 90% or 99% identity to SEQ ID NO: 1, and a second subunit comprising, or consisting of, a sequence having at least 75%, 80%, 85%, 90% or 99% identity to SEQ ID NO: 3.

In another embodiment, the functional variant comprises a first subunit comprising, or consisting of, a sequence having at least 75%, 80%, 85%, 90% or 99% identity to SEQ ID NO: 2, and a second subunit comprising, or consisting of, a sequence having at least 75%, 80%, 85%, 90% or 99% identity to SEQ ID NO: 4.

In another embodiment, the functional variant comprises a first subunit comprising, or consisting of, a sequence having at least 75%, 80%, 85%, 90% or 99% identity to SEQ ID NO: 2, and a second subunit comprising, or consisting of, a sequence having at least 75%, 80%, 85%, 90% or 99% identity to SEQ ID NO: 18.

In a further embodiment, the functional variant comprises a first subunit comprising, or consisting of, SEQ ID NO: 1 or 2, and a second subunit comprising, or consisting of, a sequence having at least 75%, 80%, 85%, 90% or 99% identity to SEQ ID NO: 3 or 4. In particular, the functional variant may comprise a first subunit comprising, or consisting of, SEQ ID NO: 1, and a second subunit comprising, or consisting of, a sequence having at least 75%, 80%, 85%, 90% or 99% identity to SEQ ID NO: 3, or may comprise a first subunit comprising, or consisting of, SEQ ID NO: 2, and a second subunit comprising, or consisting of, a sequence having at least 75%, 80%, 85%, 90% or 99% identity to SEQ ID NO: 4. The functional variant may also comprise a first subunit comprising, or consisting of, SEQ ID NO: 2, and a second subunit comprising, or consisting of, a sequence having at least 75%, 80%, 85%, 90% or 99% identity to SEQ ID NO: 18.

In another embodiment, the functional variant comprises a first subunit comprising, or consisting of, a sequence having at least 75%, 80%, 85%, 90% or 99% identity to SEQ ID NO: 1 or 2, and a second subunit comprising, or consisting of, SEQ ID NO: 3 or 4. In particular, the functional variant may comprise a first subunit comprising, or consisting of, a sequence having at least 75%, 80%, 85%, 90% or 99% identity to SEQ ID NO: 1, and a second subunit comprising, or consisting of, SEQ ID NO: 3, or may comprise a first subunit comprising, or consisting of, a sequence having at least 75%, 80%, 85%, 90% or 99% identity to SEQ ID NO: 2, and a second subunit comprising, or consisting of, SEQ ID NO: 4. The functional variant may also comprise a first subunit comprising, or consisting of, a sequence having at least 75%, 80%, 85%, 90% or 99% identity to SEQ ID NO: 2, and a second subunit comprising, or consisting of, SEQ ID NO: 18.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as (see Worldwide Website: blast.ncbi.nlm.nih.gov/) or (see Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend =0.5, End gap penalty=false, End gap open=10 and End gap extend=0.5.

The anti-neovascularization activity of the protein used in the present invention may be assessed by any method known by the skilled person. For instance, this activity may be assessed as described in examples, in particular using ex vivo models of neovascularization such as aortic or choroidal explants (see below example 1).

Functional variants may include natural variants resulting from gene polymorphism as well as artificial variants.

In an embodiment, functional variants are derived from wild-type amino acids sequences (e.g. SEQ ID NO: 1 to 4) by the introduction of one or more mutations (deletion, insertion and/or substitutions) at specific amino acid positions. Mutations may be introduced in the first subunit, the second subunit, or in both.

In particular, functional variants may comprise a first subunit comprising, or consisting of, a sequence having from 1 to 30, 1 to 25, 1 to 20, 1 to 15, 1 to 10, 1 to 5, 1 to 4, 1 to 3, or 1 or 2 modified (e.g., deleted, substituted or inserted) amino acid residues as compared to the reference sequence, i.e. SEQ ID NO: 1 or 2, and/or a second subunit comprising, or consisting of, a sequence having from 1 to 30, 1 to 25, 1 to 20, 1 to 15, 1 to 10, 1 to 5, 1 to 4, 1 to 3, or 1 or 2 modified (e.g., deleted, substituted or inserted) amino acid residues as compared to the reference sequence, i.e. SEQ ID NO: 3 or 4. More particularly, the functional variants may comprise a first subunit comprising, or consisting of, a sequence having from 1 to 30, 1 to 25, 1 to 20, 1 to 15, 1 to 10, 1 to 5, 1 to 4, 1 to 3, or 1 or 2 modified (e.g., deleted, substituted or inserted) amino acid residues as compared to SEQ ID NO: 2, and/or a second subunit comprising, or consisting of, a sequence having from 1 to 30, 1 to 25, 1 to 20, 1 to 15, 1 to 10, 1 to 5, 1 to 4, 1 to 3, or 1 or 2 modified (e.g., deleted, substituted or inserted) amino acid residues as compared to SEQ ID NO: 4.

Preferably, the functional variants may comprise a first subunit comprising, or consisting of, a sequence having from 1 to 15, 1 to 10, 1 to 5, 1 to 4, 1 to 3, or 1 or 2 modified (e.g., deleted, substituted or inserted) amino acid residues as compared to SEQ ID NO: 2, and/or a second subunit comprising, or consisting of, a sequence having from 1 to 15, 1 to 10, 1 to 5, 1 to 4, 1 to 3, or 1 or 2 modified (e.g., deleted, substituted or inserted) amino acid residues as compared to SEQ ID NO: 4. More particularly, the second subunit may comprise, or consists of, a sequence having from 1 to 15, 1 to 10, 1 to 5, 1 to 4, 1 to 3, or 1 or 2 modified (e.g., deleted, substituted or inserted) amino acid residues as compared to SEQ ID NO: 18. As described below, modifications are preferably conservative substitutions.

In a particular embodiment, the functional variant is substantially homologous to wild-type lebecetin (e.g. SEQ ID NO: 1 to 4).

Two amino acid sequences are "homologous", "substantially homologous" or "substantially similar" when one or more amino acid residues are replaced by a biologically similar residue, i.e. conservative substitution.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

As such, it should be understood that in the context of the present invention, a conservative substitution is recognized in the art as a substitution of one amino acid for another amino acid that has similar properties. Examples of conservative substitutions are set out in the Table 1 below:

TABLE 1 conservative substitutions

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr ( T) |
| Tyr (Y) | Trp (W), Phe (F), Thr (T), Ser (S) |
| Val (V) | Ile (I), Leu (L), Met (M), Phe (F), Ala (A) |

In an embodiment, the functional variant comprises a first subunit comprising, or consisting of, a sequence derived from SEQ ID NO: 1 or 2 and comprising from 1 to 30, 1 to 25, 1 to 20, 1 to 15, 1 to 10, 1 to 5, 1 to 4, 1 to 3, or 1 or 2 amino acid conservative substitutions, and/or a second subunit comprising, or consisting of, a sequence derived from SEQ ID NO: 3 or 4 and comprising from 1 to 30, 1 to 25, 1 to 20, 1 to 15, 1 to 10, 1 to 5, 1 to 4, 1 to 3, or 1 or 2 amino acid conservative substitutions. In particular, the functional variant may comprise a first subunit comprising, or consisting of, a sequence derived from SEQ ID NO: 2 and comprising from 1 to 30, 1 to 25, 1 to 20, 1 to 15, 1 to 10, 1 to 5, 1 to 4, 1 to 3, or 1 or 2 amino acid conservative substitutions, and/or a second subunit comprising, or consisting of, a sequence derived from SEQ ID NO: 4 and comprising from 1 to 30, 1 to 25, 1 to 20, 1 to 15, 1 to 10, 1 to 5, 1 to 4, 1 to 3, or 1 or 2 amino acid conservative substitutions.

In a preferred embodiment, the functional variant comprises a first subunit comprising, or consisting of, a sequence derived from SEQ ID NO: 1 and comprising from 1 to 5, preferably 1 or 2, amino acid conservative substitutions, and a second subunit comprising, or consisting of, a sequence derived from SEQ ID NO: 3 and comprising from 1 to 5, preferably 1 or 2, amino acid conservative substitutions.

In another preferred embodiment, the functional variant comprises a first subunit comprising, or consisting of, a sequence derived from SEQ ID NO: 2 and comprising from 1 to 5, preferably 1 or 2, amino acid conservative substitutions, and a second subunit comprising, or consisting of, a sequence derived from SEQ ID NO: 4 and comprising from 1 to 5, preferably 1 or 2, amino acid conservative substitutions. More particularly, the functional variant comprises a first subunit comprising, or consisting of, a sequence derived from SEQ ID NO: 2 and comprising from 1 to 5, preferably 1 or 2, amino acid conservative substitutions, and a second subunit comprising, or consisting of, a sequence derived from SEQ ID NO: 18 and comprising from 1 to 5, preferably 1 or 2, amino acid conservative substitutions.

Preferably, some residues important for lebecetin activity are conserved in the functional variant. In particular, residues corresponding to 1) cysteine residues involved in intra or inter disulfide bridges between alpha and beta chains, i.e. Cys27, Cys38, Cys55, Cys106, Cys129, Cys149 and Cys 154 of SEQ ID NO: 1, and Cys27, Cys38, Cys55, Cys100, Cys123, Cys136 and Cys 144 of SEQ ID NO: 3 (Jebali et al. 2009); and/or 2) residues of HCY domains, i.e. His37, Cys38, Tyr39 of SEQ ID NO: 1 and His37, Cys38, Tyr39 of SEQ ID NO: 3 (Jebali et al. 2009); and/or 3) residues of DAEK (SEQ ID NO: 19) domains, i.e. Asp50, Ala51, Glu52 and lys53 of SEQ ID NO: 1 and Asp50, Ala51, Glu52 and lys53 of SEQ ID NO: 3 (Jebali et al. 2009); and/or 4) residues of WIGL (SEQ ID NO: 20) motifs, i.e. Trp94 to Leu96 of SEQ ID NO: 1 and Trp94 to Leu96 of SEQ ID NO: 3 (Zelensky et al., 2005).

Preferably, all residues identified in 1), 2), 3 and 4) subsections are conserved in the functional variant.

Residues corresponding to the above identified residues of lebecetin may be easily identified by the skilled person based on any routine alignment method.

The N- and/or C-terminal ends of the protein used in the present invention described herein may be optionally protected against proteolysis. For instance, the N-terminus may be in the form of an acetyl group, and/or the C-terminus may be in the form of an amide group. Internal modifications of the protein to be resistant to proteolysis are also envisioned, e.g. wherein at least a —CONH— peptide bond is modified and replaced by a (CH2NH) reduced bond, a (NHCO) retro-inverso bond, a (CH2—O) methylene-oxy bond, a (CH2—S) thiomethylene bond, a (CH2CH2) carba bond, a (CO—CH2) cetomethylene bond, a (CHOH—CH2) hydroxyethylene bond, a (N—N) bound, a E-alcene bond or also a —CH=CH— bond.

For instance, the protein may be modified by acetylation, acylation, amidation, crosslinking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The proteins used according to the invention may comprise or be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains followed by chemical crosslinking of the chains, according to the so-called "staple" technology described in Walensky et al, 2014. For instance, amino acids at position i and i+4 to i+7 can be substituted by non-natural aminoacids that show reactive olefinic residues. All these proteolysis-resistant chemically-modified proteins are encompassed in the present invention.

The protein used in the present invention may also be covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. Protein half-life may also be increased by including the protein in a biodegradable and biocompatible polymer material for drug delivery system forming microspheres. Polymers and copolymers are, for instance, poly(D,L-lactide-co-glycolide) (PLGA) (as illustrated in US2007/0184015, Hahn S K et al).

Lebecetin can be isolated from M. lebetina venom. Lebecetin or functional variants or fragments thereof may also be obtained by recombinant techniques known to those skilled in the art. In this case, a nucleic acid and/or a genetic construct comprising, or consisting of, a nucleotide sequence encoding the first subunit and a nucleotide sequence encoding the second subunit of the protein may be expressed in a host cell and the protein may be extracted from these host cells or from the culture medium. One example of recombinant technique is described in Jebali et al. 2012. Briefly, cDNA of each subunit (e.g. SEQ ID NO: 2 and 4) was cloned into pAMoA-GD3 vectors comprising signal peptide sequence derived from the human granulocyte colony-stimulating factor. The cDNA encoding the alpha-subunit and beta-subunit may be prepared by PCR using sequences encoding MVLA1 (SEQ ID NO: 1) and MVLB1 (SEQ ID NO: 3), respectively.

The protein used in the present invention can also be synthesized using standard synthetic methods known to those skilled in the art, for example chemical synthesis or enzymatic synthesis. Examples of chemical synthesis technologies are solid phase synthesis and liquid phase.

As a solid phase synthesis, for example, the amino acid corresponding to the C-terminus of the protein to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the proteins are released, the protein chain is thus extended in this manner. Solid phase synthesis methods are largely classified by the tBoc method and the Fmoc method, depending on the type of protective group used. Typically used protective groups include tBoc (tbutoxycarbonyl), Cl—Z (2-chlorobenzyloxycarbonyl), Br—Z (2-bromobenzyloyycarbonyl), Bzl (benzyl), Fmoc (9-fluorenylmcthoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired protein, it is subjected to the de-protection reaction and cut out from the solid support. Such protein cutting reaction may be carried with hydrogen fluoride or tri-fluoromethane sulfonic acid for the Boc method, and with TFA for the Fmoc method.

The protein used according to the invention may also be administered in the form of at least one encoding nucleic acid. In an embodiment, the two subunits are encoded by the same nucleic acid. In another embodiment, the two subunits are encoded by distinct nucleic acids.

Preferably, encoding nucleic acid(s) is(are) encompassed in a genetic construct, i.e. an expression cassette, further comprising regulatory sequences (such as a suitable promoter(s), enhancer(s), terminator(s), etc.) allowing the expression (e.g. transcription and translation) of the encoded protein (the protein used in the present invention) in a host cell. The genetic construct may be DNA or RNA, preferably cDNA, and is preferably double-stranded DNA. The genetic construct may be in a form suitable for transformation of the intended host cell or host organism, in a form suitable for integration into the genomic DNA of the intended host cell or in a form suitable for independent replication, maintenance and/or inheritance in the intended host organism.

For instance, the genetic construct may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, the genetic construct comprises i) nucleic acid(s) encoding the protein used in the present invention operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a preferred embodiment, nucleic acid(s) encoding the protein used in the present invention are carried by a viral vector for ex vivo or in vivo infection and expression of said protein.

Preferably, the vector is a recombinant integrating or non-integrating viral vector. Examples of recombinant viral vectors include, but not limited to, vectors derived from herpes virus, retroviruses, lentivirus, vaccinia viruses, adenoviruses, adeno-associated viruses or bovine papilloma virus.

Preferably, nucleic acid(s) encoding the protein used in the present invention, or the genetic construct defined above, is contained in a recombinant adenovirus, adeno-associated virus or lentivirus vector.

In a preferred embodiment, the vector is a recombinant adeno-associated virus (AAV) vector.

The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVSI, located on chromosome 19 (19ql3.3-qter). Therefore AAV has arisen considerable interest as a potential vector for human gene therapy. Among the favorable properties of the virus are its lack of association with any human disease, its ability to infect both dividing and non-dividing cells, and the wide range of cell lines derived from different tissues that can be infected.

As used herein, the term "AAV vector" refers to a polynucleotide vector comprising one or more heterologous sequences (i.e., nucleic acid sequence not of AAV origin, e.g. a sequence encoding the protein used in the present invention) that are flanked by at least one AAV inverted terminal repeat sequence (ITR), preferably two ITRs. Such AAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). An "inverted terminal repeat" or "ITR" sequence is a term well understood in the art and refers to relatively short sequences found at the termini of viral genomes which are in opposite orientation. An "AAV inverted terminal repeat (ITR)" sequence is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C and D regions), allowing intra-strand base-pairing to occur within this portion of the ITR. AAV ITRs may have a wild-type nucleotide sequence or may be altered by the insertion, deletion or substitution. The serotype of the inverted terminal repeats (ITRs) of the AAV vector may be selected from any known human or nonhuman AAV serotype.

The viral vector may be packaged into a virus capsid to generate a "viral particle". In particular, the vector may be an AAV vector packaged into an AAV-derived capsid to generate an "adeno-associated viral particle" or "AAV particle" composed of at least one AAV capsid protein and an encapsidated AAV vector genome.

The capsid serotype determines the tropism range of the AAV particle. Multiple serotypes of adeno-associated virus (AAV), including 12 human serotypes and more than 100 serotypes from nonhuman primates have now been identified (Howarth al., 2010, Cell Biol Toxicol 26: 1-10). Among these serotypes, human serotype 2 was the first AAV developed as a gene transfer vector. Other currently used AAV serotypes include, but are not limited to, AAV1, AAV3, AAV4, AAV5, AAV6, AAV7, AAV8, AAVrh8, AAV9, AAV10, AAVrh10, AAV11, AAV12, AAVrh74 and AAVdj, etc.

In a particular embodiment, the AAV vector comprises an AAV-derived capsid selected from the group consisting of AAV2, AAV9, AAV9-2YF, AAV5, AAV2-7m8 (Dalkara D et al. Gene Ther. 2012 February; 19(2):176-81; Dalkara D et al. Sci Transl Mes. 2013 Jun. 12; 5(189):189ra76) or AAV8 capsid.

In addition, non-natural engineered variants and chimeric AAV can also be useful. In particular, the capsid proteins may be variants comprising one or more amino acid substitutions to enhance transduction efficiency, to minimize immunogenicity, to tune stability and particle lifetime, for efficient degradation and/or for accurate delivery to the nucleus. Mutated AAV capsids may be obtained from capsid modifications inserted by error prone PCR and/or peptide insertion or by including one or several amino acids substitutions. In particular, mutations may be made in any one or more of tyrosine residues of natural or non-natural capsid proteins (e.g. VP1, VP2, or VP3). Preferably, mutated residues are surface exposed tyrosine residues. Exemplary mutations include, but are not limited to tyrosine-to-phenyl-alanine substitutions such as Y252F, Y272F, Y444F, Y500F, Y700F, Y704F, Y730F, Y275F, Y281F, Y508F, Y576F, Y612G, Y673F and Y720F.

Alternatively to using AAV natural serotypes, artificial AAV serotypes may also be used including, without limitation, AAV with a non-naturally occurring capsid protein. Such an artificial capsid may be generated by any suitable technique, using a selected AAV sequence (e.g., a fragment of a VPI capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid or a mutated AAV capsid. A chimeric capsid comprises VP capsid proteins derived from at least two different AAV serotypes or comprises at least one chimeric VP protein combining VP protein regions or domains derived from at least two AAV serotypes. An AAV particle can comprise viral proteins and viral nucleic acids of the same serotype or a mixed serotype (i.e. pseudotyped AAV). For example, the recombinant AAV vector may be an AAV serotype 2/1 hybrid recombinant gene delivery system comprising AAV2 genome and AAV1 capsid proteins. Those skilled in the art are familiar with such vectors and methods for their construction and use, see e.g. WO 01/83692. The AAV vector for use in the present invention may be easily chosen by the skilled person.

The present invention relates to a protein selected from lebecetin, and functional variants and fragments thereof, as well as nucleic acids, vectors or viral particles as described above and encoding said protein, for use in the treatment of neovascular disease.

As used herein, the term "treatment", "treat" or "treating" refers to any act intended to ameliorate the health status of patients such as therapy and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

As used herein, the term "subject" or "patient" refers to an animal preferably to a mammal, even more preferably to a human, including adult, child and human at the prenatal stage.

In particular, the term "treatment of neovascular disease" may refer to the diminution of pathological and excessive neoangiogenesis, i.e. pathological neovascularisation.

As used herein, the term "neovascular disease" refers to any disease with a neovascular component, i.e. involving neovascularization (pathological neoangiogenesis). Examples of such diseases include, but are not limited to, ocular neovascular diseases, cancers and inflammatory disorders with a neovascular component.

In an embodiment, the neovascular disease is an ocular neovascular disease (i.e. ocular disease with a neovascular component), preferably selected from the group consisting of age-related macular degeneration, diabetic retinopathies such as diabetic retinal ischemia or proliferative diabetic retinopathy, iris neovascularization, intraocular neovascularization, corneal neovascularization, retinal neovascularization, choroidal neovascularization, corneal inflammation (in particular due to keratitis, ocular herpes or herpes zoster).

In a further embodiment, the disease is a cancer with a neovascular component. The cancer is preferably a solid cancer. It may be a primary or metastatic cancer, preferably selected from the group consisting of lung, breast, gastric, colorectal, pancreas and brain cancers. In particular, the neovascular component of the cancer may refer to tumor neovascularization and/or activation or upregulation of genes or signaling pathways known to be associated with tumor angiogenesis such as VEGF signaling pathway.

In another embodiment, the disease is an inflammatory disorder with neovascular component, preferably selected from the group consisting of rheumatoid arthritis, psoriasis, osteoarthritis, inflammatory bowel disease, Crohn's disease and ulcerative colitis.

In a further aspect, the present invention also provides a pharmaceutical composition comprising a protein used in the present invention (i.e. lebecetin, or a functional variant or fragment thereof), or a nucleic acid, vector or viral particle as described above and encoding said protein, and a pharmaceutically acceptable excipient. Preferably, the present invention also relates to the pharmaceutical composition of the invention for use in the treatment of neovascular disease.

It also relates to the use of a protein used according to the present invention (i.e. lebecetin, or a functional variant or fragment thereof), or a nucleic acid, vector or viral particle as described above and encoding said protein, or a pharmaceutical composition of the invention, for the manufacture of a medicament for the treatment of a neovascular disease.

All the embodiments described above are also contemplated in this aspect.

In an embodiment, the pharmaceutical composition comprises a protein used according to the present invention, i.e. lebecetin or a functional variant or fragment thereof, and a pharmaceutically acceptable excipient.

In another embodiment, the pharmaceutical composition comprises a nucleic acid, vector or viral particle encoding a protein used according to the present invention (i.e. lebecetin or a functional variant or fragment thereof) and as described above, and a pharmaceutically acceptable excipient.

The pharmaceutically acceptable excipient is selected according to the route of administration and the nature of the active ingredient, e.g. a protein, a nucleic acid or a viral particle. As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolality, encapsulating agents, pH buffering substances, and buffers. Such excipients include any pharmaceutical agent suitable for direct delivery to the eye which may be administered without undue toxicity.

Possible pharmaceutical compositions include those suitable for oral, rectal, topical (including transdermal, buccal, sublingual, ocular instillation), intraocular (including intravitreal, intracameral, subretinal, suprachoroidal, periocular, subconjunctival) or parenteral (including subcutaneous, intramuscular, intraspinal, intravenous and intradermal) administration. For these formulations, conventional excipient can be used according to techniques well known by those skilled in the art. Preferably, the pharmaceutical composition is suitable for parenteral or ocular administration. More preferably, the pharmaceutical composition is suitable for ocular administration including topical ocular instillation and intraocular administration.

The compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For ocular administration, the composition can be formulated with one or more pharmaceutically acceptable sterile isotonic aqueous or nonaqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

The pharmaceutical composition may comprise several proteins used according to the present invention (i.e. selected from lebecetin, and functional variants or fragments thereof), and/or nucleic acids, vectors or viral particles as described above and encoding said proteins.

The pharmaceutical composition may also comprise at least one another active compound, in particular selected from the group consisting of angiogenesis inhibitors, anti-inflammatory drugs, antineoplastic agents, anti-bacterial agents and anti-viral agents.

Examples of angiogenesis inhibitors include, but are not limited to, anti-VEGF (vascular endothelial growth factor) agents such as antibodies directed to VEGF or VEGF receptor (e.g., bevacizumab, ranibizumab, DC101), small molecules that bind to and inhibit VEGF receptors (e.g., SU6668, TSU68, aflibercept), tyrosine kinase inhibitors (e.g., axitinib, sunitnib, sorafenib, and pazopanib), PI3K inhibitors (e.g., PI-103), EGFR inhibitors (e.g. gefitinib, erlotinib), Ras inhibitors (FTIs), AKT inhibitors (e.g. nelfinavir), anti-SFRP2 antibodies, angiostatin, endostatin, and metastatin. Preferably, the angiogenesis inhibitor is an inhibitor of the VEGF pathway, in particular aflibercept.

Examples of anti-inflammatory drugs, include, but are not limited to, non-steroid anti-inflammatory drugs (NSAIDs) such as salicylates (e.g. acetylsalicylic acid), propionic acid derivatives (e.g. ibuprofen, ketoprofen), acetic acid derivatives (e.g. indomethacin, aceclofenac), enolic acid derivatives (e.g. piroxicam, meloxicam, tenoxicam), anthranilic acid derivatives (e.g. mefenamic acid) and selective COX-2 inhibitors (e.g. celecoxib).

An "antineoplastic agent" is an agent with anti-cancer activity that inhibits or halts the growth of cancerous cells or immature pre-cancerous cells, kills cancerous cells or immature pre-cancerous cells, increases the susceptibility of cancerous or pre-cancerous cells to other antineoplastic agents, and/or inhibits metastasis of cancerous cells. These agents may include chemical agents as well as biological agents. Examples include, without limitation, 5-aza-2'deoxycytidine, 17-AAG (17-N-Allylamino-17-demethoxygeldanamycin), tretinoin (ATRA), bortezomib, cisplatin, carboplatin, oxaliplatin, paclitaxel, bevacizumab, tamoxifen, leucovorin, docetaxel, transtuzumab, etoposide, flavopiridol, 5-fluorouracil, irinotecan, TRAIL (TNF-related apoptosisinducing ligand), LY294002, PD184352, perifosine, Bay 11-7082, gemcitabine, bicalutamide, zoledronic acid, cis-retinoic acid, MK-0457, imatinib, desatinib, sorafenib, temozolomide, actinomycin, anthracyclines, doxorubicin, daunorubicin, valrubicine, idarubicine, epirubicin, bleomycin, plicamycin and mitomycin.

Examples of anti-bacterial agents include, but are not limited to, penicillins, aminoglycosides, macrolides, monobactams, rifamycins, tetracyclines, chloramphenicol, clindamycin, lincomycin, imipenem, fusidic acid, novobiocin, fosfomycin, fusidate sodium, neomycin, polymyxin, capreomycin, colistimethate, colistin, gramicidin, minocycline, doxycycline, vanomycin, bacitracin, kanamycin, gentamycin, erythromicin and cephalosporins.

Examples of anti-viral agents include, but are not limited to, alpha-methyl-Padamantane methylamine, 1-D-ribofuranosyl-1,2,4-triazole-3 carboxamide, 9-(2-hydroxyethoxy) methylguanine, adamantanamine, 5-iodo-2'-deoxyuridine, trifluorothymidine, interferon, adenine arabinoside, CD4, 3'-azido-3'-deoxythymidine (AZT), 9-(2-hydroxyethoxymethyl)-guanine (acyclovir), phosphonoformic acid, 1-adamantanamine, peptide T, and 2',3'dideoxycytidine.

In a particular embodiment, the pharmaceutical composition comprises at least one another active compound that is selected from the group consisting of angiogenesis inhibitors, anti-inflammatory drugs and anti-neoplastic agents.

In a preferred embodiment, the pharmaceutical composition comprises at least one another active compound that is an angiogenesis inhibitor, preferably an inhibitor of the VEGF pathway, more preferably aflibercept. In particular, the pharmaceutical composition may comprise a protein comprising a first subunit comprising, or consisting of, the amino acid sequence of SEQ ID NO: 1 or SEQ ID NO: 2, and a second subunit comprising, or consisting of, the amino acid sequence of SEQ ID NO: 3 or SEQ ID NO: 4, and an angiogenesis inhibitor, preferably an inhibitor of the VEGF pathway, more preferably aflibercept. More particularly, the pharmaceutical composition may comprise a protein comprising a first subunit comprising, or consisting of, the amino acid sequence of SEQ ID NO: 2, and a second subunit comprising, or consisting of, the amino acid sequence of SEQ ID NO: 4, and an angiogenesis inhibitor, preferably an inhibitor of the VEGF pathway, more preferably aflibercept.

The amount of pharmaceutical composition of the invention to be administered has to be determined by standard procedure well known by those of ordinary skill in the art.

Physiological data of the patient (e.g. age, size, and weight), the routes of administration and the disease to be treated have to be taken into account to determine the appropriate dosage. The appropriate dosage of the pharmaceutical composition of the invention may also vary if it is used alone or in combination.

The pharmaceutical composition may be administered as a single dose or in multiple doses, preferably a single dose.

In a particular embodiment, the pharmaceutical composition is intended to be used in the treatment of an ocular disease and each unit dosage may contain, for example, from 0.1 to 12 mg per eye, preferably from 1 to 5 mg per eye.

The pharmaceutical composition according to the invention may be used alone or in combination with another therapy, in particular with an angiogenesis inhibitor, an anti-inflammatory drug, antineoplastic agent, an anti-bacterial agent and/or an anti-viral agent, preferably with an angiogenesis inhibitor, an anti-inflammatory drug or antineoplastic agent.

In particular, when used in combination with the pharmaceutical composition of the invention, antineoplastic agents may include radiotherapeutic agents such as X-rays, gamma rays, alpha particles, beta particles, photons, electrons, neutrons, radioisotopes, and other forms of ionizing radiation.

Preferably, the pharmaceutical composition is used in combination with an angiogenesis inhibitor, more preferably an inhibitor of the VEGF pathway, even more preferably aflibercept.

In a particular embodiment, the pharmaceutical composition is used to treat a subject who does not respond or became resistant to a therapy with an angiogenesis inhibitor, preferably an inhibitor of the VEGF pathway, more preferably aflibercept.

In a further aspect, the present invention further concerns a method for treating a neovascular disease, comprising administering a therapeutically efficient amount of the pharmaceutical composition of the invention in a subject in need thereof.

All the embodiments described above are also contemplated in this aspect.

By a "therapeutically efficient amount" is intended an amount of the pharmaceutical composition administered to a subject that is sufficient to prevent or inhibit new blood vessel formation, i.e. to prevent or inhibit neoangiogenesis, and in particular pathological neoangiogenesis, and/or to allow regression of neovascularization.

In a preferred embodiment, the subject in need thereof is a subject who does not respond or became resistant to a therapy with an angiogenesis inhibitor, preferably an inhibitor of the VEGF pathway, more preferably aflibercept.

In a further aspect, the present invention also concerns lebecetin, a functional variant or fragment thereof, a nucleic acid, vector or viral particular encoding lebecetin or functional variant or fragment thereof, or a pharmaceutical composition of the invention, for use as neovascularization inhibitor.

The present invention also concerns lebecetin, a functional variant or fragment thereof, a nucleic acid, vector or viral particular encoding lebecetin or functional variant or fragment thereof, or a pharmaceutical composition of the invention, for use to prevent, inhibit or regress neovascularization in a subject in need thereof.

The following examples are given for purposes of illustration and not by way of limitation.

EXAMPLES

Materials and Methods

Animals

Three and eleven weeks-old C57BL/6JRj male mice and 4-days-old Lewis rat pups were purchased from Janvier Labs (Le Genest-Saint-Isle, France). Eleven weeks-old CX3CR1$^{+/GFP}$ male mice were obtained from the Jackson Laboratory (Bar Harbor, USA). Animals were housed in the animal facility under specific pathogen-free condition, in a 12/12 h light/dark cycle with water and normal diet food available ad libitum.

All procedures were performed in accordance with the guidelines from Directive 2010/63/EU of the European Parliament on the protection of animals used for scientific purposes and approved by the Institutional Animal Care and Use Committee, Comité d'éthique pour l'expérimentation animale Charles Darwin (N° 02371.02).

Vascular Sprouting from Aortic Ring Ex Vivo

After decapitation of Lewis rat pups, thoracic aortas were cut into 1-mm-thick rings and covered with 15 µl of growth factor-reduced phenol red free matrigel (Corning, Boulogne Billancourt, France) in 48 well tissue culture plates. Aortic rings were cultured for 3 days in Dulbecco's Modified Eagle's Medium (DMEM) (Thermo Fisher Scientific, Villebon-sur-Yvette, France) supplemented with 10% fetal bovine serum, 1% penicillin/streptomycin, and 0.2% fungizone (Lavalette, S. et al. 2011). Explants were exposed to LCT isolated from M. lebetina venom at different doses (30 nM, 300 nM, 1.5 µM) from day 3 (D3) to D6 of culture. Control explants were cultured in DMEM without addition of LCT. Photographs of individual explants were taken from D3 to D6. The surface of each individual aortic ring and pre-incubation sprouts at D3 was subtracted from the surface at D6 to calculate the vascular sprouting that occurred in the presence or absence of LCT. The areas of sprouting were quantified with Fiji software (Schindelin, J. et al. 2012). Data are expressed as the percentage of growth between D6 and D3.

Vascular Sprouting from Choroid Ex Vivo

Eyes were enucleated from C57BL/6JRj mice and kept in ice-cold endothelium growth medium (EGM-2) (Lonza, Levallois-Perret, France) before dissection. Choroid was separated from the other eye tissues and cut into approximately 1 mm×1 mm. Choroid fragments were isolated and placed in growth factor-reduced phenol red free matrigel (Corning, Boulogne Billancourt, France) seeded in 48 well plates.

Choroidal explants were then cultured for 3 days in EGM-2 medium supplemented with 5% fetal bovine serum, 1% penicillin/streptomycin, and 0.2% fungizone in a 37° C. cell culture incubator (Shao, Z. et al. 2013). On D3, Choroid fragments were treated with LCT (1.5 nM, 5 µM, 15 µM) isolated from M. lebetina venom or recombinant LCT (1.5 µM, 5 µM, 10 µM) from D3 until D6 of culture. Photos of individual explants were taken and the areas of sprouting were quantified with Fiji software (Schindelin, J. et al. 2012). The surface of each individual choroidal explant and pre-incubation sprouts at D3 was subtracted from the surface at D6 to calculate the vascular sprouting that occurred in the presence or absence of LCT.

SD-OCT

Pupils were dilated with tropicamide (Mydriaticum) (Thea, Clermont-Ferrand, France) and phenylephrin (Neosynephrine) (Europhta, Monaco). Mice were then anesthetized by inhalation of isoflurane (2%) (Axience, Pantin, France) and placed in front of the spectral domain optical coherence tomography (SD-OCT) imaging device (Bioptigen 840 nm HHP; Bioptigen, N.C., USA). Images were acquired from optic disc at approximately 0.1 or 1.4 mm of the superior retina. SD-OCT was calibrated (1 pixel=1.6 µm) as previously described (Dominguez, E. et al. 2015). Retinal layer, inner nuclear layer (INL), outer nuclear layer (ONL) and photoreceptor outer segments (OS) thicknesses were measured at 500 µm from the centre of the optic nerve at day 7 by FIJI software (Schindelin, J. et al. 2012).

Electroretinography (ERG)

ERG was performed 7 days after injection of PBS and LCT isolated from *M. lebetina* venom (500 µM). C57BL/6JRj mice were kept overnight for dark adaptation and then anesthetized with an intraperitoneal injection of ketamine (100 mg/kg, Virbac, Carros, France) and xylazine (10 mg/kg, Bayer HealthCare, Berlin,Germany). Pupils were dilated with phenylephrin (Neosynephrine) (Europhta, Monaco) and tropicamide (Mydriaticum) (Théa, Clermont-Ferrand, France). The cornea was anesthetized with oxybuprocaine chlorhydrate (Théa, Clermont-Ferrand, France). Body temperature was maintained at 37° C. using a heating pad. Upper and lower lids were retracted to keep eyes open and bulging. A gold-loop electrode was placed in contact with the surface of each cornea and maintained with lubrithal (Zubial, Auros, France) to record ERG (Espion, Diagnosys LLC, Lowell, Mass., USA). Reference and ground electrodes were respectively placed in the forehead and in the back of animal. The light stimulus was provided by Ganzfeld stimulator (Espion, Diagnosys LLC, Lowell, Mass., USA). Responses were amplified and filtered (1 Hz-low and 300 Hz-high cut off filters) with a 1 channel DC/AC-amplifier. Five levels of stimulus intensity (0.003 cd.s/m$^2$; 0.03 cd.s/m$^2$; 0.3 cd.s/m$^2$; 3 cd.s/m$^2$; 10 cd.s/m$^2$) were used for scotopic ERG recording. Each scotopic ERG response represents the average of five responses from a set of five flashes of stimulation.

To evaluate cone responses, mice were exposed 5 minutes to the light at 20 cd/m$^2$ to saturate rod photoreceptors. A 10 cd.s/m$^2$ level of stimulus intensity was used for the light adapted ERGs. The light adapted ERGs were recorded on the same rod-suppressive white background as for the light adaptation. Each cone photopic ERG response represents the average of ten responses to a set of ten consecutive flashes. The flicker ERG was also used to isolate cone responses at flash frequencies of 10 and 20 Hz at 1 cd.s/m$^2$ intensity.

Laser-Induced Choroidal Neovascularization (CNV) Model

C57BL/6JRj mice were anesthetized with an intraperitoneal injection of ketamine (100 mg/kg, Virbac, Carros, France) and xylazine (10 mg/kg, Bayer HealthCare, Berlin, Germany). Pupils were dilated and 4 laser coagulations (400 mW, 50 ms, 100 µm spot size) were performed with a Laser Yag 532 Eyelite (Alcon, Rueil-Malmaison, France) mounted on a slit lamp (BQ900, Hagg-Streitt, Chambery, France). Laser photocoagulation and rupture of Bruch's membrane were confirmed by immediate observation of a bubble (Lavalette, S. et al. 2011, Berger, A. et al. 2014). Mice were injected with 1 µl of PBS, LCT isolated from *M. lebetina* venom (500 µM), recombinant LCT (500 µM) or Aflibercept (25 µM) immediately or 3 days after laser.

7 days after lesion, retinas of mice were examined with SD-OCT. OCT sequences were acquired and analyzed with Fiji (Schindelin, J. et al. 2012). Lesion volume was calculated with the formula $(4/3\pi * a * b^2)/2$, where a is the polar radius that corresponds to the measure along the vertical axis and b is the equator radius that corresponds to the horizontal axis (Berger, A. et al. 2014).

On D7, mice were euthanized by CO2 inhalation and CNV areas were quantified on immunostained choroidal flatmounts with MetaMorph software (Molecular Devices, Saint-Gregoire, France).

Oxygen-Induced Retinopathy (OIR) Model

C57BL/6JRj pups mice with nursing mothers were exposed to 75% oxygen at postnatal day (P) 7 for 5 consecutive days as previously reported (Connor, K. M. et al. 2009). On P12, mice were returned to room-air and injected intravitreally with PBS, LCT isolated from *M. lebetina* venom (500 µM) or recombinant LCT (500 µM) or Aflibercept (25 µM). At P17 mice were sacrificed by $CO_2$ inhalation and retinas were dissected. Vaso-obliteration (VO) and neovascularization (NV) areas were calculated on flatmounted immunostained retinas with MetaMorph software (Molecular Devices, Saint-Gregoire, France).

RT-qPCR

Integrin subunits αv, α5, ß3 and ß5 gene expression was quantified by reverse transcription quantitative polymerase chain reaction (RT-qPCR) in CNV model at days 0, 1, 3 and 7 after laser injury. Choroids were dissected in RNase-free conditions. Total RNA was isolated with Nucleospin RNAII (Macherey Nagel, Hoerdt, France). Single-stranded cDNA was synthesized from total RNA (pretreated with DNaseI amplification grade, Thermo Fisher Scientific, Villebon-sur-Yvette, France) using oligo-dT as a primer and superscript II reverse transcriptase (Thermo Fisher Scientific, Villebon-sur-Yvette, France). Real-time polymerase chain reaction was performed using cDNA and SYBR Green Gene Expression Master Mix (Thermo Fisher Scientific, Villebon-sur-Yvette, France) and the following primers (0.5 pmol/µl) (Life Technologies, Saint-Aubin, France): GAPDH sense: 5'-ACG GCC GCA TCT TCT TGT GCA-3' (SEQ ID NO: 5); GAPDH antisense: 5'-CAG GCG CCC AAT ACG GCC AA-3' (SEQ ID NO: 6); ITGAV sense: 5'-CAC CCT CAG AGA GGG AGA TG-3' (SEQ ID NO: 7); ITGAV antisense: 5'-ACG TAC AGG ATT GCG CTC TT-3' (SEQ ID NO: 8); ITGA5 sense: 5'-AGT ACG CAC CTT GCC GCT CA-3' (SEQ ID NO: 9); ITGA5 antisense: 5'-ACA CGG CCA GTC TTG GTG AAC-3' (SEQ ID NO: 10); ITGB3 sense: 5'-AAC CGG GGA ACG CTC CAT GA-3' (SEQ ID NO: 11); ITGB3 antisense: 5'-CGG CGT TTT TGC CAG TAT CCG-3' (SEQ ID NO: 12); ITGB5 sense: 5'-AGC CTT TGG GGA GAC GTG TGA-3' (SEQ ID NO: 13); ITGB5 antisense: 5'-TGG TGG TGG CAG GTC TGG TT-3' (SEQ ID NO: 14).

PCR reactions were performed in 45 cycles of 15 s at 95° C., 45 s at 60° C. Data were normalized to GAPDH and expressed relative to control group values.

Reagents and Drugs

LCT was obtained as previously described (Sarray, S. et al. 2003). Briefly, venom of *M. lebetina* was gel-filtrated using Sephadex G-75 Column. Firstly, LCT was purified by FPLC on a Mono S (HR5/5) column and eluted with linear 0-1 M NaCl gradient. LCT was lyophilized and next dissolved in PBS. LCT preparation quality was tested on C8 reversed phase HPLC column with linear gradient of acetonitrile (Sarray, S. et al. 2003). Aflibercept (Eylea; Bayer, Lyon, France) was kindly provided by Dr Chiara Eandi (University of Torino) and Dr Audrey Giocanti-Aurégan (Hopital Avicenne Paris). For in vivo studies 1 µl of the following solution were injected in the vitreous: 500 µM LCT (15 µg/µl) or 25 µM Aflibercept (2.5 µg/µl). In some experiments, 2 µl of PBS or of labeled-LCT, -Aflibercept or -BSA were injected in the right eye.

Recombinant LCT Production

Two nucleic acid sequences encoding alpha (SEQ ID NO: 15) and beta (SEQ ID NO: 16) LCT subunits (including the peptide signal MACPGFLWALVISTCLEFSMA (SEQ ID No: 17)) have been cloned in two pCDNA3.1 (+) plasmids. Mature sequences of alpha and beta LCT subunits are SEQ ID NO: 2 and 18, respectively. Beta LCT sequence comprises 6-histidin tag in C-ter domain. HEK expi293 cells were cotransfected with the two constructs. Supernatants were harvested four days later by centrifugation 15 min at 500 g 4° C., followed by a second centrifugation 30 min at 15 900 g 4° C. and a 0.22 µm filtration before storage at −20° C. Supernatants were purified at room temperature and with endotoxin-free conditions. Supernatants were thawed and concentrated up to 300 mL and dialfiltered on tangential flow filtration (TFF) 5 kDa-0.1 m² cassettes (Centra mate serie T, PALL) with phosphate buffer (NaPO$_4$ 20 mM; NaCl 300 mM; pH 7.2). Imidazole 10 mM was added and histidine-tagged proteins were purified on Hitrap IMAC sepharose FF 5 mL (GE healthcare Life Sciences) column. Pre-equilibration and wash steps were performed with buffer 20 mM NaPO$_4$; pH 7.2; NaCl 300 mM, 10 mM Imidazole. A step of 40 mM Imidazole allowed elimination of most contaminants (other cell proteins). Elution was performed with a gradient of Imidazole from 80 to 500 mM. The optimal imidazole concentration to elute LCT is 165 mM. Eluted fractions were pooled, then concentrated and diafiltered on Vivaspin® 3 kDa (GE healthcare Life Sciences) to eliminate imidazole. Proteins were resuspended with TBS buffer (tris-HCl 20 mM; NaCl 150 mM; pH 7.5) and filtered through 0.22 µm membrane.

Labeling Proteins with Alexa Fluor® 647

Alexa Fluor® 647 microscale protein labeling Kit (Thermo Fisher Scientific, Villebon-sur-Yvette, France) was used to label LCT (500 µM), Aflibercept (25 µM) and Bovine Serum Albumin (BSA, 15.4 µM). Proteins were dissolved in 1 M sodium bicarbonate and mixed with Alexa Fluor 647 succinimidyl ester that react with primary amines of proteins and incubated for 1 h at 4° C. The conjugated protein was separated from unreacted dye using the supplied spin column at room temperature. The final concentration was estimated according to manufacturer's recommendations to ¼ of the initial concentration.

Histological Analysis 7 days after CNV and injection of PBS or 647-LCT, a 300 µL mixture of ketamine (100 mg/kg, Virbac, Carros, France) and xylazine (10 mg/kg, Bayer HealthCare, Berlin,Germany) was injected intraperitoneally to deeply anesthetized animals. Mice were perfused via the ascending aorta with 5 mL of 0.9% NaCl solution followed by 30 mL of 4% paraformaldehyde solution. After fixation, brain was carefully dissected out and post-fixed 48 h in the same fixative. Free-floating sections (40 µm) were performed using a vibratome (Leica Microsystems, Wetzlar, Germany).

Immunochemistry

Mice were euthanized by CO2 inhalation. Eyes were enucleated and fixed in 4% paraformaldehyde for 30 min at room temperature. After several washes in PBS, the cornea and lens were removed and the retina was carefully separated from RPE/choroid/sclera.

Retinal flatmounts were stained with goat polyclonal anti-collagen IV antibody (AbD Serotec, Cergy Pontoise, France) and FITC-coupled *Bandeirae simplicifolia* (BS)-1 lectin (Sigma-Aldrich, Saint Quentin Fallavier, France). Astrocytes and activated Muller cells were labeled using anti-Glial Fibrillary Acidic Protein (GFAP) antibody (Sigma-Aldrich, Saint Quentin Fallavier, France) and microglial cells were stained using rabbit polyclonal anti-Iba1 (Wako, Neuss, Germany). The RPE was stained using TRITC-coupled phalloidin (Sigma-Aldrich, Saint Quentin Fallavier, France) on choroidal flatmounts. Nuclei were stained with DAPI (Sigma-Aldrich, Saint Quentin Fallavier, France). In CNV model, neovessels were immunostained with CD102 (Rat anti-mouse, BD Biosciences Pharmingen, Le Pont de Claix, France), microglial cells were labeled using anti-Iba1 and endothelial cells nuclei were stained with DAPI on choroidal flatmounts. Brain sections were placed in a blocking solution containing 3% Normal Goat Serum and 0.1% triton X-100 for 1 h, then incubated with rabbit anti-ATF3 (Santa Cruz Biotechnology, Heidelberg, Germany) and TRITC-coupled *Bandeirae simplicifolia* (BS)-1 lectin at 4° for 48 h and stained with DAPI. In OIR model, retinal capillaries were labeled with FITC-BS-1 lectin. The corresponding Alexa-conjugated secondary antibodies (Thermo Fisher Scientific, Villebon-sur-Yvette, France) were used to reveal the primary antibodies.

Retina, choroids and brain sections were viewed with a fluorescence microscope (DM5500B) (Leica, Saint Jorioz, France) or with a confocal microscope (FV1000) (Olympus, Rungis, France). The microscope was calibrated for control mice (PBS) before acquisitions in LCT-injected mice.

Statistical Analysis

GraphPad Prism (GraphPad Software, San Diego, USA) was used for data analysis and graphic representation. All values are reported as mean±SEM. Data were analyzed by Mann-Whitney U test, one-way ANOVA followed by Bonferroni or Dunnett's post-tests. P<0.05 was considered as statistically significant.

Results

Example 1

LCT Inhibits Vascular Sprouting from Aortic and Choroidal Explants

LCT inhibits endothelial cell proliferation and tubulogenesis in vitro (Pilorget, A. et al. 2007). To test if LCT inhibits neovascularization ex vivo, we cultured mouse aortic rings in matrigel (Lavalette, S. et al. 2011). Aortic rings were cultured for 3 days to allow for vessel sprouting and then treated with increasing doses of LCT. Three days after the addition of LCT, vessel sprouting area was quantified and expressed as the increase (in percentage) of sprouting area between D3 and D6 (FIG. 1A and B). In control conditions, vascular sprouting increased by 259% between D3 and D6. LCT added at a final concentration of 30 nM did not affect vascular sprouting while 300 nM of LCT reduced vascular sprouting between D3 and D6 to 85%. LCT at a dose of 1.5 µM totally inhibited sprouting and resulted in the regression of pre-existing D3 vascular sprouts (FIG. 1B). Increasing doses of LCT did not notably affect fibroblasts that grow out of the explant and proliferate on the plastic dish cell surface. LCT activity was next tested in the mouse choroidal explant model that closely reproduces the formation of vessels from the chorio-capillary bed (Shao, Z. et al. 2013). Choroids were cultured as explants as previously described (Shao, Z. et al. 2013). As for aortic rings, explants were treated at D3 with LCT and analyzed at D6 (FIG. 1C and D). We first used the dose that resulted in vascular regression in aortic rings. At 1.5 µM LCT inhibited vessel sprouting by 78% when compared to control conditions but still allowed for a 286% increase of vessels compared to D3. At 5 µM, LCT efficiently inhibited vessel growth but failed at regressing pre-existing D3 vascular sprouts. Finally, at 15 µM, LCT induced D3 sprouts regression (FIG. 1D). LCT was thus effective at reducing vascular sprouting in two independent ex vivo models of neovascularization.

Example 2

LCT Intravitreal Injection Does Not Alter Retinal Integrity

Figure 2B:
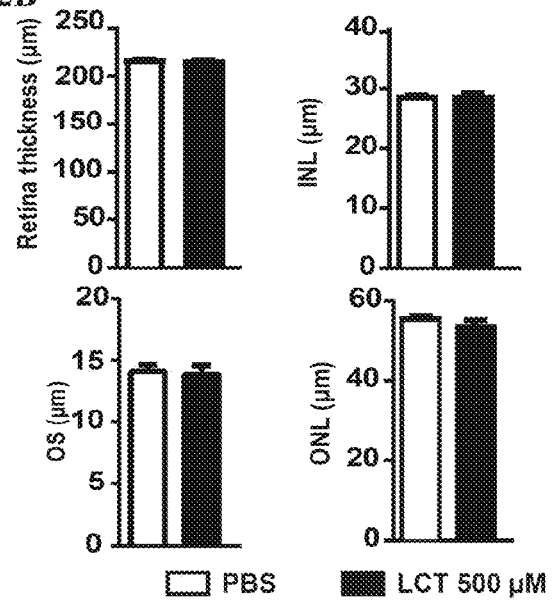
Figure 2C:
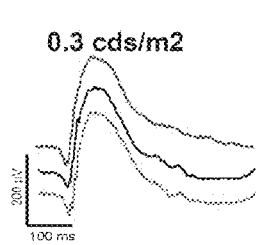
Figure 2D:
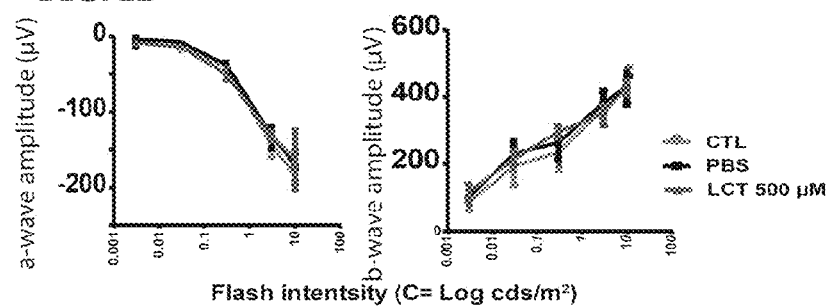
Figure 2E:
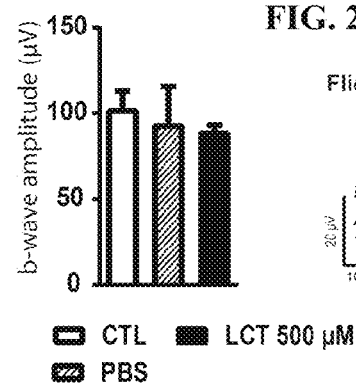
Figure 2F:
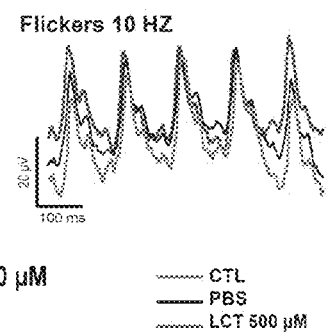
Figure 2G:
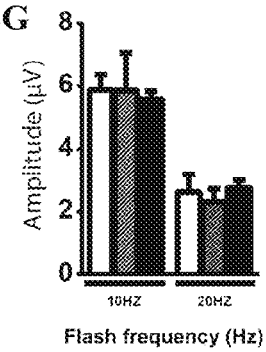

Ex vivo experiments demonstrated variability in the dose required to inhibit neovascularization. We thus ran a pilot study to determine the concentration required to reduce neovascularization in the model of laser induced choroidal neovascularization (CNV). One µl of LCT was used for intravitreal injection, as the vitreous volume is 5.3 µl (Remtulla, S. Et al. 1985), the initial concentration of LCT could be estimated to ⅕ of its initial concentration. Depending on its pharmacokinetics LCT may then reaches all ocular compartments (10 µl) and its concentration may decrease to ¹⁄₁₀ of the initial concentration. Animals were thus intravitrealy injected with 1 µl of 150 or 500 µM of LCT to reach the estimated final concentration of 15 µM (the dose that regress choroidal explant sprouts) or 50 µM (the highest concentration we can purify from venom). We determined that an intravitreal injection of 1 µl LCT at 150 µM was not sufficient to reduce CNV while a 1 µl injection of 500 µM LCT decreases the neovascular area. To test if a single injection of 500 µM LCT alters retinal architecture we injected LCT in control adult mice and examined their retina after 7 days. Retinal architecture was analyzed by SD-OCT. OCT did not reveal significant changes in the overall structure of the retina (FIG. 2A). The thickness of the entire retina, of the inner and outer nuclear layers and outer segments was not statistically different between controls and LCT injected-eyes (FIG. 2B). ERG responses were recorded from control animals and treated animals 7 days after injection. Intravitreal injections of LCT did not alter scotopic ERG recorded at intensity ranging from 0.003 to 10 cds/m$^2$ (FIG. 2C; D) when compared to control or PBS-injected animals. Similarly photopic responses (FIG. 2E) and flicker responses (FIG. 2F; G) were not altered after LCT injections when compared to control animals.

Figure 3A:
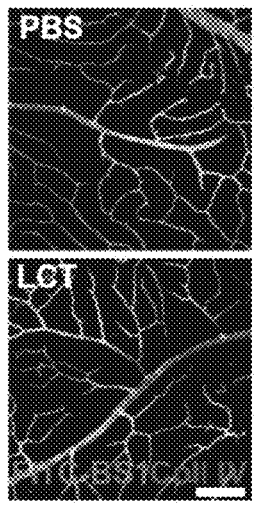
FIGS. 3A-3D: LCT intravitreal injection does not alter vascular integrity.
Figure 3B:
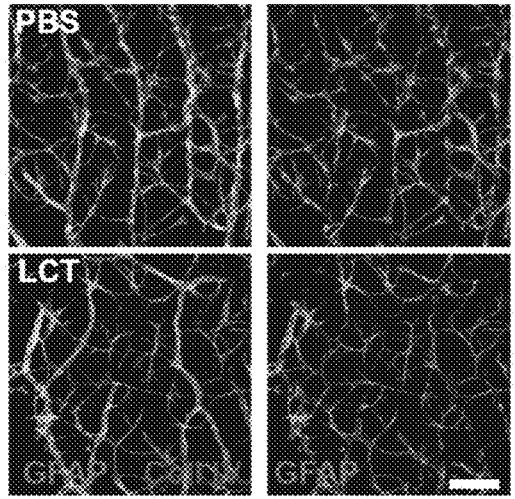
Figure 3C:
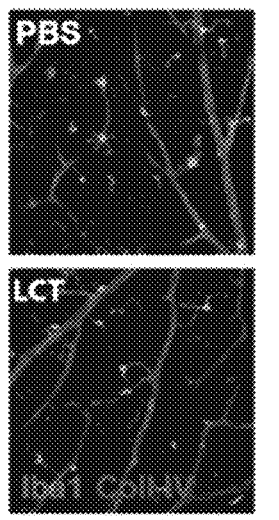
Figure 3C:
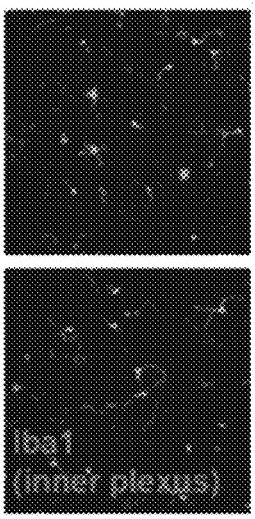
Figure 3C:
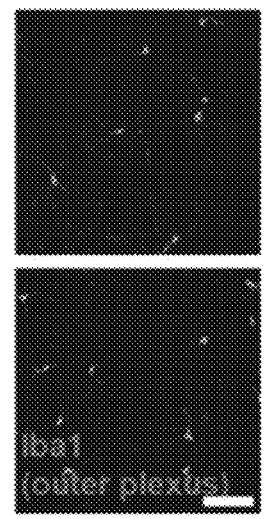
Figure 3D:
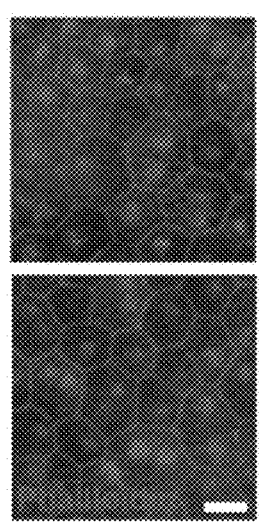

Vasculature integrity was next evaluated by immunochemistry 7 days after injection. Retinal flatmounts were stained with FITC-BS-1 lectin and collagen-IV that label respectively endothelial cells and vascular basal membranes. Ghost vessels (detected as collagen IV-positive, lectin-negative vessels) and neovascular tufts were not detected in eyes injected with LCT at 500 µM (FIG. 3A). Loss of vascular integrity results in micro- and macro-glial cell activation. Retinal flatmounts were thus immunostained with anti-GFAP (specific for astrocytes and activated Muller cells) or anti-Iba1 (specific for microglial cells) antibodies. LCT did not modify astrocyte morphology and vessel coverage and no sign of Muller cell activation was found in the inner layer of the retina one week after LCT or PBS intravitreal injection (FIG. 3B). We next examined microglial cells morphology after LCT injection in the vitreous of CX3CR1$^{+/GFP}$ mice. LCT did not modify the morphology of CX3CR1-positive cell located in the superficial or deep plexus (FIG. 3C). RPE cell morphology was assayed using TRITC-coupled phalloidin, 7 days after LCT injection. No sign of RPE cells death or alteration of RPE morphology was detected (FIG. 3D). All together our results indicated that a LCT does not alter retinal architecture, retinal function, or vessel integrity 7 days after injection.

Example 3

LCT Inhibits Laser-induced Choroidal Neovascularization

Figure 4A:
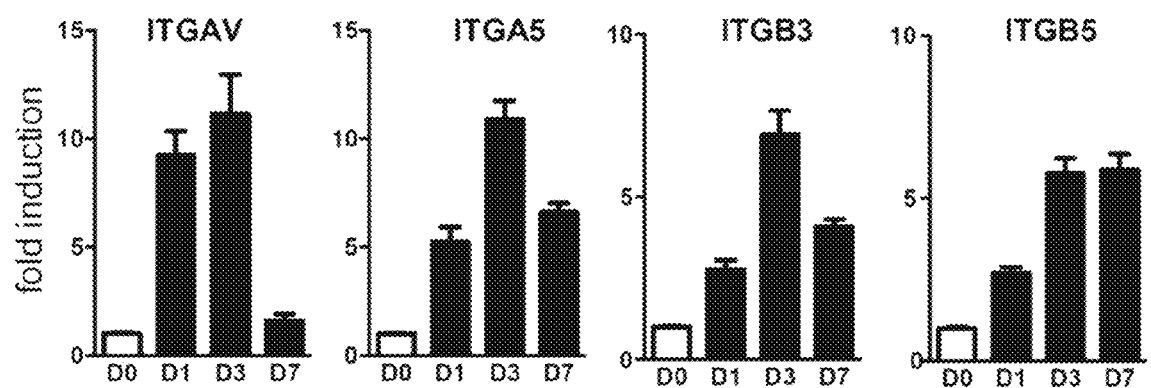
FIGS. 4A-4E: LCT binds to CNV lesions. (FIG. A) Quantitative RT-PCR of integrin subunit mRNA (αv, α5, β3, β5) normalized with GADPH mRNA of C57BL/6JRj choroids collected at days 0, 1, 3, and 7, after laser-induced choroidal lesions, n=8 eyes per group (FIGS. 4B-4E) Microphotographs of laser-induced CNV lesions at D7 on choroidal flatmounts after intravitreal injections on D4 of bovine serum albumin (647-BSA), LCT (647-LCT) or Aflibercept (647-Aflibercept) covalently conjugated to an Alexa Fluor 647 dye. All choroids were co-stained with CD102 antibody (green). Scale bars in B-E=50 µm.
Figures 4B, 4C, 4D, 4E:
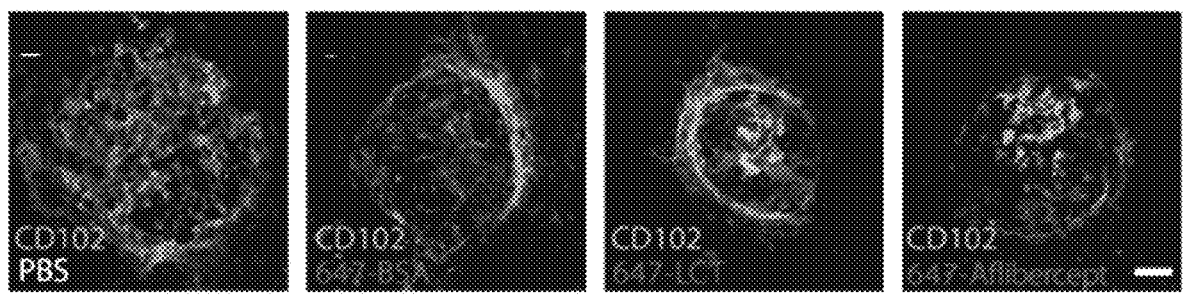

We showed that LCT inhibits HBMEC proliferation and tubulogenesis in vitro (Pilorget, S. et al. 2007) and vascular sprouting in ex vivo models of neovascularization (FIG. 1) without affecting vascular integrity (FIG. 3). To test if LCT inhibits in vivo neovascularization, LCT activity was assayed in the CNV mouse model. Integrin subunits αv and α5 has been shown recently to be increased from D3 to D7 in the rat CNV model (Nakajima, T. et al. 2014). We quantified the expression of integrin subunits αv and α5 and ß3 and ß5 in mouse choroids after laser-induced choroidal lesions at different time-points. Choroidal lesions were induced on D0 with an ophthalmic laser and choroids were collected at D1, D3 and D7. The expression of these subunits was analyzed by RT-qPCR and compared to non-lesioned choroids (D0). The expression of all subunits was found to be increased within 24h after lesion and peaked at D3. At D7, αv returned to basal level while α5, ß3 and ß5 remained elevated (FIG. 4A). To determine the specificity of LCT binding after intravitreal injections, we next injected labeled molecules in the vitreous of laser-lesioned eyes. Bovine serum albumin (BSA), LCT and Aflibercept were covalently conjugated to an Alexa Fluor 647 dye using a microscale protein labeling kit, and then purified and injected three days (D4) before sacrifice (D7) in the right eye. Left eye received a PBS injection. Alexa Fluor 647-conjugated BSA (647-BSA) did not labeled CD102-postive CNV lesions. In contrast both 647-LCT and 647-Aflibercept labeling was found in CD102-positive CNV lesions on choroidal flatmount (FIG. 4D; E). Retinal flatmounts were then labeled with Collagen-IV to detect vascular basal membranes and deposits. An intense 647-LCT labeling was found in the outer part of the retina facing the CNV lesion and a faint labeling was observed on large arteries in the LCT-injected eye. No labeling was found in the contralateral PBS-injected eye. We next analyzed 647-LCT labeling in the optic nerve, the trigeminal nerve and in different areas of the brain of 647-LCT injected animals and compared it to PBS-only injected animals. LCT was not detected in the optic and trigeminal nerve (data not shown) nor in hippocampus, piriform cortex, cingulate cortex, hypothalamus, ventromedial preoptic nucleus (VMPO) and the caudate putamen (striatum). Furthermore we did not detect ATF3 labeling indicative of neuronal injury (Launay, P. S. et al. 2016; Tsujino, H. et al. 2000).

To determine the in vivo anti-neovascularization properties of LCT, we quantified lesion volumes 7 days after laser impact as previously described (Berger, A. et al. 2014) after a single injection of LCT on D0 and compared it to PBS treated animals. LCT injection decreased the lesion volume by 31.9% when compared to controls (FIG. 5A). We next quantified the area covered by neovessels on choroidal flatmounts stained with CD102 at D7. CNV areas were significantly reduced by 26.7% 7 days after LCT injection (FIG. 5B; C). Anti-VEGF are routinely used to treat choroidal neovascularization in AMD patients (Kovach, J. L. et al. 2012). We next compared LCT to anti-VEGF. Bevacizumab and Ranibizumab commercial antibodies only recognize human VEGF, we thus used Aflibercept that binds both human and mouse VEGF (Papadopoulos, N. et al. 2012). A single injection of Aflibercept reduced choroidal neovascularization by 31.5% (FIG. 5B; C). LCT and Aflibercept-treated lesions were not statistically different in size (FIG. 5A). Subretinal mononuclear phagocytes (sMP) participate in choroidal neovascularization (Lambert, V. et al. 2013). To evaluate the effect of LCT on sMP accumulation around lesion, choroidal flatmounts were stained with the anti-Iba1 antibody that labels sMP. No difference in the number of sMP around lesion was found between LCT and PBS treated eyes. Similarly no difference in the number of sMP was found between LCT- and Aflibercept-treated lesions (FIG. 5B; D).

Integrins $\alpha v\beta 3$ and $\alpha v\beta 5$ are critical regulators of angiogenesis, we thus determined if LCT injection regulates their expression. As $\alpha v\beta 3$ and $\alpha v\beta 5$ are expressed by proliferating endothelium, we investigate the expression of $\alpha v$, $\alpha 5$, $\beta 3$ and $\beta 5$ shortly after LCT injection (24 h) to discriminate a possible transcriptional regulation from the long term anti-neovascularization effect of LCT. $\alpha v$, $\alpha 5$, $\beta 3$ and $\beta 5$ expression is maximum at D3, we thus analyze their expression on D3 after a single injection of LCT or PBS on D2. qPCR analysis did not reveal significant differences in their level of expression between LCT and PBS in RPE/choroids extracts (FIG. 5E).

We showed that high doses of LCT regresses existing vessels (FIG. 1), we thus next injected LCT in the vitreous three days after laser impacts and quantified the neovascularization size. When injected after the initial vessel growth, LCT injection allowed vascular regression by 19% (FIG. 6A; B). All together our results showed that a single injection of LCT allowed prevention and regression of choroidal neovascularization without impairing sMP recruitment.

Example 4

LCT Inhibits Retinal Neovascularization in the Oxygen Induced Retinopathy (OIR) Model We next tested the effect of LCT on retinal neovascularization, a hallmark of severe ischemic retinopathies, in the OIR model. This model has been widely used to understand retinal vascular loss, vascular regrowth, neovascularization and neovascular regression (Connor, K. M. et al. 2009). Retinal neovascularization is induced by subjecting newborn rodents to hyperoxia between P7 and P12 to inhibit physiological vascular development. When animals are returned to room air, the relative retinal hypoxia leads to severe retinal neovascularization between P12 and P17 (Smith, L. E. et al. 1994). To determine the binding specificity of LCT, we first injected Alexa Fluor 647-conjugated LCT (647-LCT) in the vitreous of OIR-subjected animals three days before their sacrifice on P17. 647-LCT intensively labeled BS-1 lectin positive neovessel tufts while retinal vasculature was not labeled (FIG. 7A). To evaluate the anti-angiogenic properties of LCT in the OIR model, P7 mice were subjected to OIR and injected with 1 μl of PBS or 500 μM LCT on day 12 and were returned to room-air. Mice were sacrificed at P17 and vaso-obliteration (VO) and neovascularization area (NV) were determined on retinal flatmount stained with BS-1 lectin as previously described (Stahl, A. et al. 2009). LCT did not change the ratio of VO when compared to PBS injection (FIG. 7B; D). In contrast, a single injection of LCT at P12 reduced the area covered by retinal neovascularization at P17 by 48.1% (FIG. 7B; E). To compare LCT treatment to the anti-VEGF therapy, 25 μM of Aflibercept was injected at P12, a dose that has been shown to reduce NV without affecting retinal development Stahl, A. et al. 2009) and NV and VO were compared to LCT animals. No differences were found in VO and NV between LCT and Aflibercept treatments (FIG. 7B-E).

Example 5

Figures 8A, 8B:
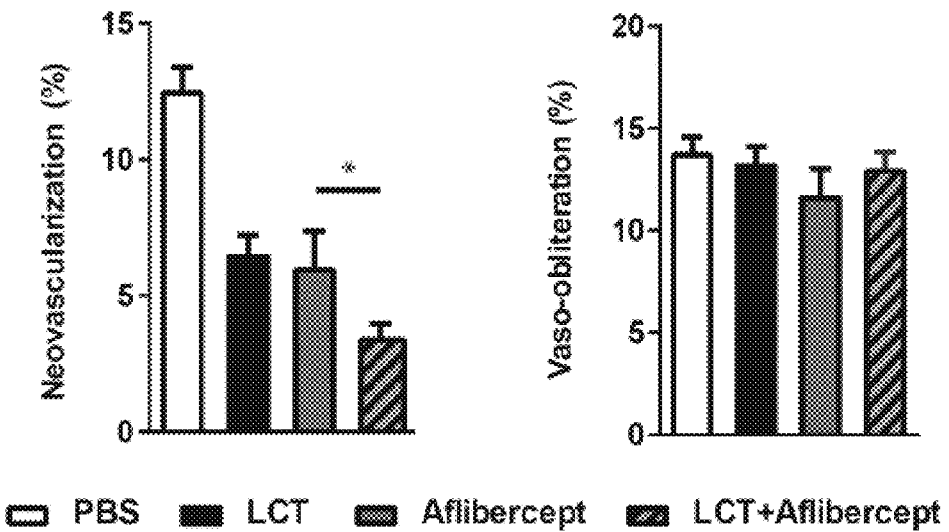
FIGS. 8A-8B.

Co-Injection of LCT and Aflibercept Results in Greater Neovascularization Inhibition than Aflibercept Alone We next tested the effect of co-injection of LCT and Aflibercept on retinal neovascularization in the OIR model. To evaluate the anti-angiogenic properties of co-injection of LCT and Aflibercept in the OIR model, P7 mice were subjected to OIR and injected with 1 μL of PBS, 500 μM LCT, 25 μM Aflibercept or 500 μM LCT and 25 μM Aflibercept on day 12 and were returned to room-air. Mice were sacrificed at P17 and vaso-obliteration (VO) and neovascularization area (NV) were determined on retinal flatmount stained with BS-1 lectin. Co-injection of LCT and aflibercept did not change the ratio of VO when compared to PBS (FIG. 8). In contrast, co-injection of LCT and Aflibercept results in a greater neovascularization inhibition than Aflibercept or LCT alone.

Example 6

Recombinant LCT Inhibits Vascular Sprouting from Choroidal Explants

Figure 9A:
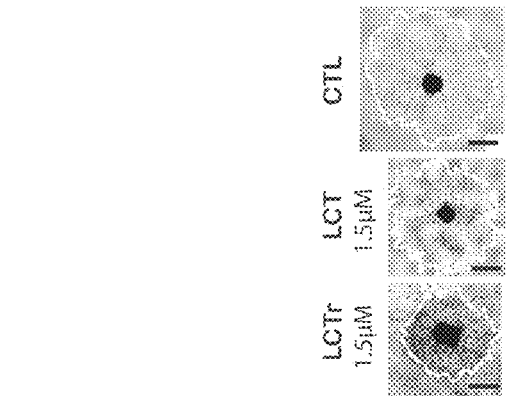
FIGS. 9A-9C.
Figures 9B, 9C:
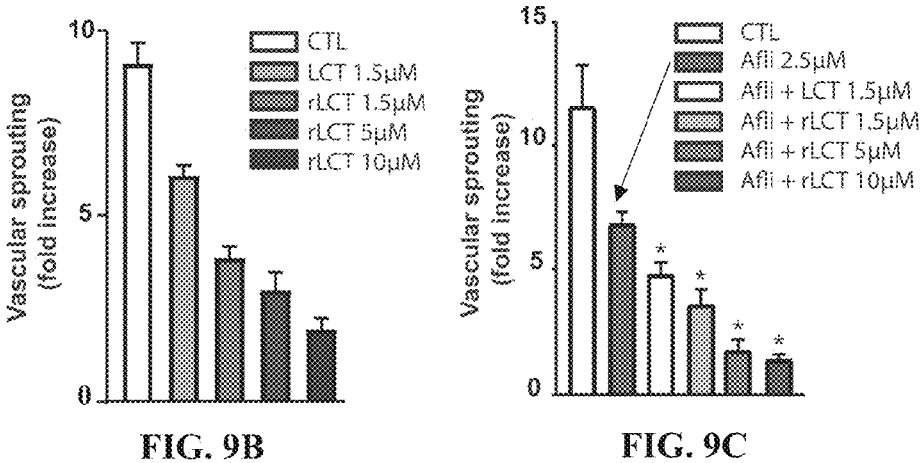

Recombinant LCT activity was tested in the mouse choroidal explant model that closely reproduces the formation of vessels from the chorio-capillary bed (Shao, Z. et al. 2013). Choroids were cultured as explants as previously described (Shao, Z. et al. 2013). Explants were treated at D3 with recombinant LCT (rLCT) and analyzed at D6 (FIG. 9). At 1.5 μM rLCT inhibited vessel sprouting by 65.0% when compared to control conditions.

Example 7

Figure 10A:
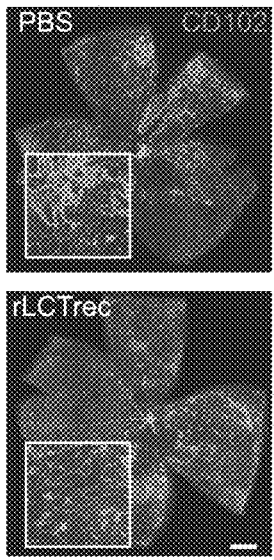
FIGS. 10A-10C.
Figure 10B:
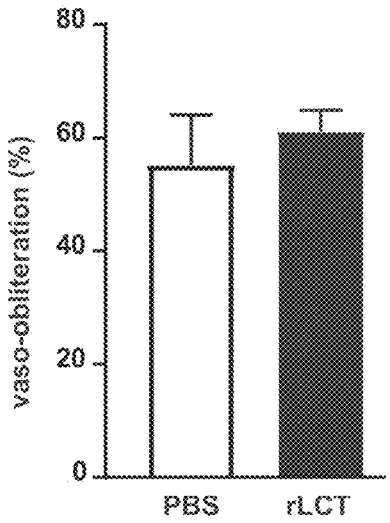
Figure 10C:
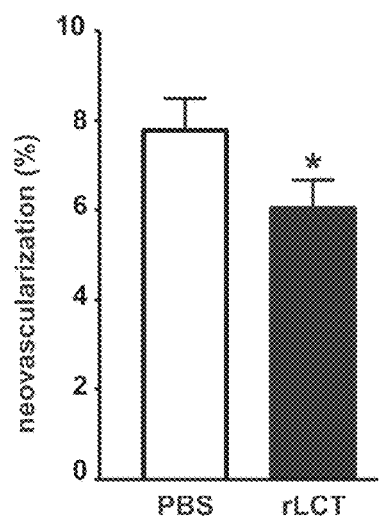

Recombinant LCT Inhibits Retinal Neovascularization in the Oxygen Induced Retinopathy (OIR) Model We next tested the effect of recombinant LCT on retinal neovascularization, a hallmark of severe ischemic retinopathies, in the OIR model. Retinal neovascularization is induced by subjecting newborn rodents to hyperoxia between P7 and P12 to inhibit physiological vascular development. When animals are returned to room air, the relative retinal hypoxia leads to severe retinal neovascularization between P12 and P17 (Smith, L. E. et al. 1994). To evaluate the anti-angiogenic properties of rLCT in the OIR model, P7 mice were subjected to OIR and injected with 1 μl of PBS or 500 μM rLCT on day 12 and were returned to room-air. Mice were sacrificed at P17 and vaso-obliteration (VO) and neovascularization area (NV) were determined on retinal flatmount stained with BS-1 lectin as previously described (Stahl, A. et al. 2009) (FIG. 10A). rLCT did not change the ratio of VO when compared to PBS injection (FIG. 10B). In contrast, a single injection of rLCT at P12 reduced the area covered by retinal neovascularization at P17 by 22.1% (FIG. 10C).

Example 8

Recombinant LCT Inhibits Laser-Induced Choroidal Neovascularization

Figure 11A:
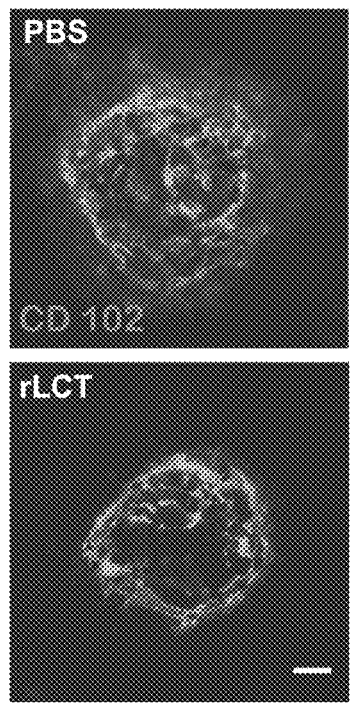
FIGS. 11A-11B.
Figure 11B:
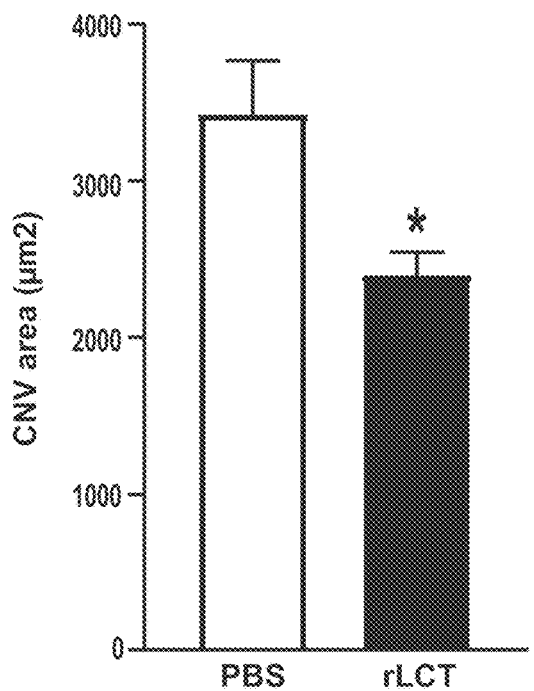

To test if recombinant LCT inhibits in vivo neovascularization, rLCT activity was assayed in the CNV mouse model. Choroidal lesions were induced on D0 with an ophthalmic laser and choroids were collected at D7. To determine the in vivo anti-neovascularization properties of rLCT, we quantified the area covered by neovessels on choroidal flatmounts stained with CD102 at D7 (FIG. 11A). CNV areas were significantly reduced by 29.8% 7 days after rLCT injection (FIG. 11B).

REFERENCES

Berger, A., Cavallero, S., Dominguez, E., Barbe, P., Simonutti, M., Sahel, J.-A., Sennlaub, F., Raoul, W., Paques, M., and Bemelmans, A.-P. (2014) Spectral-Domain Optical Coherence Tomography of the Rodent Eye: Highlighting Layers of the Outer Retina Using Signal Averaging and Comparison with Histology. PLoS One 9, e96494

Bishop, P. N. (2015) The role of extracellular matrix in retinal vascular development and preretinal neovascularization. Exp. Eye Res. 133, 30-36

Brooks, P. C., Montgomery, A. M., Rosenfeld, M., Reisfeld, R. A., Hu, T., Klier, G., and Cheresh, D. A. (1994) Integrin alpha v beta 3 antagonists promote tumor regression by inducing apoptosis of angiogenic blood vessels. Cell 79, 1157-1164

Brown, D. M., Kaiser, P. K., Michels, M., Soubrane, G., Heier, J. S., Kim, R. Y., Sy, J. P., and Schneider, S., ANCHOR Study Group. (2006) Ranibizumab versus verteporfin for neovascular age-related macular degeneration. N. Engl. J. Med. 355, 1432-1444

Connor, K. M., Krah, N. M., Dennison, R. J., Aderman, C. M., Chen, J., Guerin, K. I., Sapieha, P., Stahl, A., Willett, K. L., and Smith, L. E. H. (2009) Quantification of oxygen-induced retinopathy in the mouse: a model of vessel loss, vessel regrowth and pathological angiogenesis. Nat. Protoc. 4, 1565-1573

D'Amore, P. A. (1994) Mechanisms of retinal and choroidal neovascularization. Invest. Ophthalmol. Vis. Sci. 35, 3974-3979

Dominguez, E., Raoul, W., Calippe, B., Sahel, J.-A., Guillonneau, X., Paques, M., and Sennlaub, F. (2015) Experimental Branch Retinal Vein Occlusion Induces Upstream Pericyte Loss and Vascular Destabilization. PLoS One 10, e0132644

Eghøj, M. S. and Sørensen, T. L. (2012) Tachyphylaxis during treatment of exudative age-related macular degeneration with ranibizumab. Br. J. Ophthalmol. 96, 21-23

Forooghian, F., Cukras, C., Meyerle, C. B., Chew, E. Y., and Wong, W. T. (2009) Tachyphylaxis Following Intravitreal Bevacizumab for Exudative Age-Related Macular Degeneration. Retina Phila. Pa 29, 723-731

Friedlander, M., Brooks, P. C., Shaffer, R. W., Kincaid, C. M., Varner, J. A., and Cheresh, D. A. (1995) Definition of two angiogenic pathways by distinct alpha v integrins. Science 270, 1500-1502

Friedlander, M., Theesfeld, C. L., Sugita, M., Fruttiger, M., Thomas, M. A., Chang, S., and Cheresh, D. A. (1996) Involvement of integrins alpha v beta 3 and alpha v beta 5 in ocular neovascular diseases. Proc. Natl. Acad. Sci. U. S. A. 93, 9764-9769

Friedman, D. S., O'Colmain, B. J., Muñoz, B., Tomany, S. C., McCarty, C., de Jong, P. T. V. M., Nemesure, B., Mitchell, P., and Kempen, J., Eye Diseases Prevalence Research Group. (2004) Prevalence of age-related macular degeneration in the United States. Arch. Ophthalmol. Chic. Ill 1960 122, 564-572

Fu, Y., Ponce, M. L., Thill, M., Yuan, P., Wang, N. S., and Csaky, K. G. (2007) Angiogenesis inhibition and choroidal neovascularization suppression by sustained delivery of an integrin antagonist, EMD478761. Invest. Ophthalmol. Vis. Sci. 48, 5184-5190

Goodman, S. L. and Picard, M. (2012) Integrins as therapeutic targets. Trends Pharmacol. Sci. 33, 405-412

Honda, S., Nagai, T., and Negi, A. (2009) Anti-angiogenic effects of non-peptide integrin alphavbeta3 specific antagonist on laser-induced choroidal neovascularization in mice. Graefes Arch. Clin. Exp. Ophthalmol. Albrecht Von Graefes Arch. Für Klin. Exp. Ophthalmol. 247, 515-522

Jebali J, Bazaa A, Sarray S, Benhaj K, Karboul A, El Ayeb M, Marrakchi N, Gargouri A. (2009) C-type lectin protein isoforms of *Macrovipera lebetina*: cDNA cloning and genetic diversity. Toxicon. February; 53(2):228-37.

Jebali J., Jeanneau C., Morjen M., Mathieu S., Bazaa A., El Ayeb M., Luis J.,Gargouri A., Marrakchi N., el Battari A. (2012) Expression of a functional recombinant C-type lectin-like protein lebecetin in the human embryonic kidney cells. Biotechnol Prog. 2012 November-December; 28(6): 1560-5

Kempen, J. H., O'Colmain, B. J., Leske, M. C., Haffner, S. M., Klein, R., Moss, S. E., Taylor, H. R., and Hamman, R. F., Eye Diseases Prevalence Research Group. (2004) The prevalence of diabetic retinopathy among adults in the United States. Arch. Ophthalmol. Chic. Ill 1960 122,552-563

Klein, R., Peto, T., Bird, A., and Vannewkirk, M. R. (2004) The epidemiology of age-related macular degeneration. Am. J. Ophthalmol. 137,486-495

Kovach, J. L., Schwartz, S. G., Flynn, H. W., and Scott, I. U. (2012) Anti-VEGF Treatment Strategies for Wet AMD. J. Ophthalmol. 2012

Lambert, V., Lecomte, J., Hansen, S., Blacher, S., Gonzalez, M.-L. A., Struman, I., Sounni, N. E., Rozet, E., de Tullio, P., Foidart, J. M., Rakic, J.-M., and Noel, A. (2013) Laser-induced choroidal neovascularization model to study age-related macular degeneration in mice. Nat. Protoc. 8,2197-2211

Launay, P.-S., Reboussin, E., Liang, H., Kessal, K., Godefroy, D., Rostene, W., Sahel, J.-A., Baudouin, C., Melik Parsadaniantz, S., and Reaux Le Goazigo, A. (2016) Ocular inflammation induces trigeminal pain, peripheral and central neuroinflammatory mechanisms. Neurobiol. Dis. 88, 16-28

Lavalette, S., Raoul, W., Houssier, M., Camelo, S., Levy, O., Calippe, B., Jonet, L., Behar-Cohen, F., Chemtob, S., Guillonneau, X., Combadière, C., and Sennlaub, F. (2011) Interleukin-1β Inhibition Prevents Choroidal Neovascularization and Does Not Exacerbate Photoreceptor Degeneration. Am. J. Pathol. 178, 2416-2423

Martinez-Zapata, M. J., Martí-Carvajal, A. J., Solà, I., Pijoán, J. I., Buil-Calvo, J. A., Cordero, J. A., and Evans, J. R. (2014) Anti-vascular endothelial growth factor for proliferative diabetic retinopathy. Cochrane Database Syst. Rev. 11, CD008721

Nakajima, T., Hirata, M., Shearer, T. R., and Azuma, M. (2014) Mechanism for laser-induced neovascularization in rat choroid: Accumulation of integrin α chain-positive cells and their ligands. Mol. Vis. 20, 864-871

Papadopoulos, N., Martin, J., Ruan, Q., Rafique, A., Rosconi, M. P., Shi, E., Pyles, E. A., Yancopoulos, G. D., Stahl, N., and Wiegand, S. J. (2012) Binding and neutralization of vascular endothelial growth factor (VEGF) and related ligands by VEGF Trap, ranibizumab and bevacizumab. Angiogenesis 15, 171-185

Pilorget, A., Conesa, M., Sarray, S., Michaud-Levesque, J., Daoud, S., Kim, K. S., Demeule, M., Marvaldi, J., El Ayeb, M., Marrakchi, N., Béliveau, R., and Luis, J. (2007) Lebectin, a *Macrovipera lebetina* venom-derived C-type lectin, inhibits angiogenesis both in vitro and in vivo. J. Cell. Physiol. 211, 307-315

Remtulla, S. and Hallett, P. E. (1985) A schematic eye for the mouse, and comparisons with the rat. Vision Res. 25, 21-31

Robbins, S. G., Brem, R. B., Wilson, D. J., O'Rourke, L. M., Robertson, J. E., Westra, I., Planck, S. R., and Rosenbaum, J. T. (1994) Immunolocalization of integrins in proliferative retinal membranes. Invest. Ophthalmol. Vis. Sci. 35, 3475-3485

Rosenfeld, P. J., Brown, D. M., Heier, J. S., Boyer, D. S., Kaiser, P. K., Chung, C. Y., and Kim, R. Y., MARINA Study Group. (2006) Ranibizumab for neovascular age-related macular degeneration. N. Engl. J. Med. 355, 1419-1431

Salehi-Had, H., Roh, M. I., Giani, A., Hisatomi, T., Nakao, S., Kim, I. K., Gragoudas, E. S., Vavvas, D., Guccione, S., and Miller, J. W. (2011) Utilizing Targeted Gene Therapy with Nanoparticles Binding Alpha v Beta 3 for Imaging and Treating Choroidal Neovascularization. PLoS One 6, e18864

Sarray, S., Srairi, N., Hatmi, M., Luis, J., Louzir, H., Regaya, I., Slema, H., Marvaldi, J., El Ayeb, M., and Marrakchi, N. (2003) Lebecetin, a potent antiplatelet C-type lectin from *Macrovipera lebetina* venom. Biochim. Biophys. Acta 1651, 30-40

Sarray, S., Delamarre, E., Marvaldi, J., El Ayeb, M., Marrakchi, N., and Luis, J. (2007) Lebectin and lebecetin, two C-type lectins from snake venom, inhibit alpha5beta1 and alphaV-containing integrins. Matrix Biol. J. Int. Soc. Matrix Biol. 26, 306-313

Schindelin, J., Arganda-Carreras, I., Frise, E., Kaynig, V., Longair, M., Pietzsch, T., Preibisch, S., Rueden, C., Saalfeld, S., Schmid, B., Tinevez, J.-Y., White, D. J., Hartenstein, V., Eliceiri, K., Tomancak, P., and Cardona, A. (2012) Fiji: an open-source platform for biological-image analysis. Nat. Methods 9, 676-682

Shao, Z., Friedlander, M., Hurst, C. G., Cui, Z., Pei, D. T., Evans, L. P., Juan, A. M., Tahir, H., Duhamel, F., Chen, J., Sapieha, P., Chemtob, S., Joyal, J.-S., and Smith, L. E. H. (2013) Choroid Sprouting Assay: An Ex Vivo Model of Microvascular Angiogenesis. PLoS One 8, e69552

Smith, L. E., Wesolowski, E., McLellan, A., Kostyk, S. K., D'Amato, R., Sullivan, R., and D'Amore, P. A. (1994) Oxygen-induced retinopathy in the mouse. Invest. Ophthalmol. Vis. Sci. 35, 101-111

Stahl, A., Connor, K. M., Sapieha, P., Willett, K. L., Krah, N. M., Dennison, R. J., Chen, J., Guerin, K. I., and Smith, L. E. H. (2009) Computer-aided quantification of retinal neovascularization. Angiogenesis 12, 297-301

Tsujino, H., Kondo, E., Fukuoka, T., Dai, Y., Tokunaga, A., Miki, K., Yonenobu, K., Ochi, T., and Noguchi, K. (2000) Activating transcription factor 3 (ATF3) induction by axotomy in sensory and motoneurons: A novel neuronal marker of nerve injury. Mol. Cell. Neurosci. 15, 170-182

Umeda, N., Kachi, S., Akiyama, H., Zahn, G., Vossmeyer, D., Stragies, R., and Campochiaro, P. A. (2006) Suppression and Regression of Choroidal Neovascularization by Systemic Administration of an α5β1 Integrin Antagonist. Mol. Pharmacol. 69, 1820-1828

Walensky L. D., Bird G. H. (2014) Hydrocarbon-stapled peptides: principles, practice, and progress. J Med Chem. 2014 Aug. 14; 57(15):6275-88

Wang, W., Wang, F., Lu, F., Xu, S., Hu, W., Huang, J., Gu, Q., and Sun, X. (2011) The antiangiogenic effects of integrin alpha5beta1 inhibitor (ATN-161) in vitro and in vivo. Invest. Ophthalmol. Vis. Sci. 52, 7213-7220

Zahn, G., Vossmeyer, D., Stragies, R., Wills, M., Wong, C. G., Löffler, K. U., Adamis, A. P., and Knolle, J. (2009) Preclinical evaluation of the novel small-molecule integrin alpha5beta1 inhibitor JSM6427 in monkey and rabbit models of choroidal neovascularization. Arch. Ophthalmol. Chic. Ill 1960 127, 1329-1335 Zelensky et al. FEBS Journal, 2005, 272: 6179-6217

The invention claimed is:

1. A method of treating an ocular neovascular disease in a subject in need thereof, said method comprising administering to the subject having an ocular neovascular disease a protein having anti-neovascularisation activity or a pharmaceutical composition comprising said protein, said protein comprising:
- a first subunit comprising, or consisting of, the amino acid sequence SEQ ID NO: 1 or SEQ ID NO: 2, or a functional variant or fragment thereof having at least 99% sequence identity thereto, and
- a second subunit comprising, or consisting of, the amino acid sequence SEQ ID NO: 3 or SEQ ID NO: 18 or SEQ ID NO: 4, or a functional variant or fragment thereof having at least 99% sequence identity thereto.

2. The method of claim 1, wherein said protein is lebecetin.

3. The method of claim 1, wherein
the first subunit comprises, or consists of, the amino acid sequence SEQ ID NO: 1 or 2, or a functional variant or fragment thereof having at least 99% sequence identity thereto, and
the second subunit comprises, or consists of, the amino acid sequence SEQ ID NO: 3 or 4, or a functional variant or fragment thereof having at least 99% sequence identity thereto.

4. The method of claim 1, wherein
the first subunit comprises, or consists of, the amino acid sequence SEQ ID NO: 2, or a functional variant or fragment thereof having at least 99% sequence identity thereto, and
the second subunit comprises, or consists of, the amino acid sequence SEQ ID NO: 4, or a functional variant or fragment thereof having at least 99% sequence identity thereto.

5. The method of claim 1, wherein the first subunit comprises, or consists of, a sequence having from 1 to 2 deleted, substituted or inserted amino acid residues as compared to SEQ ID NO: 1 or SEQ ID NO: 2, and/or the second subunit comprises, or consists of, a sequence having from 1 to 2 deleted, substituted or inserted amino acid residues as compared to SEQ ID NO: 3 or SEQ ID NO: 4.

6. The method of claim 5, wherein the substitutions of the amino acid are amino acid conservative substitutions.

7. The method of claim 1, wherein said protein is a functional variant of lebecetin and wherein residues corresponding to:
1) cysteine residues involved in intra or inter disulfide bridges between alpha and beta chains; and/or
2) residues of HCY domains; and/or
3) residues of DAEK (SEQ ID NO: 19) domains; and/or
4) residues of WIGL (SEQ ID NO: 20) motifs, are conserved.

8. The method of claim 1, said pharmaceutical composition further comprising at least one additional active substance.

9. The method of claim 1, wherein: a) said composition is used in combination with at least one angiogenesis inhibitor; or b) said composition further comprises at least one angiogenesis inhibitor.

10. The method of claim 9, wherein said angiogenesis inhibitor is an inhibitor of the VEGF pathway that is aflibercept.

11. The method of claim 9, wherein said angiogenesis inhibitor is an inhibitor of the VEGF pathway.

12. The method of claim 1, wherein said ocular neovascular disease is selected from the group consisting of age-related macular degeneration, diabetic retinopathies, diabetic retinal ischemia, proliferative diabetic retinopathy, iris neovascularization, intraocular neovascularization, corneal neovascularization, retinal neovascularization, choroidal neovascularization and corneal inflammation.

13. The method of claim 1, wherein the subject to be treated does not respond or became resistant to a therapy with an angiogenesis inhibitor.

14. The method of claim 1, wherein the two subunits are linked by disulfide bridges, thereby forming a heterodimer.

15. The method of claim 1, wherein:
the first subunit comprises SEQ ID NO: 2,
the second subunit comprises SEQ ID NO: 4 or SEQ ID NO: 18, and
the two subunits are linked by disulfide bridges, thereby forming a heterodimer.

16. The method of claim 1, wherein:
the first subunit consists of SEQ ID NO: 2,
the second subunit consists of SEQ ID NO: 4 or SEQ ID NO: 18, and
the two subunits are linked by disulfide bridges, thereby forming a heterodimer.

17. The method of claim 1, wherein said protein is a functional variant of lebecetin and wherein the following residues are conserved:
1) Cys27, Cys38, Cys55, Cys106, Cys129, Cys149 and Cys 154 of SEQ ID NO: 1, and Cys27, Cys38, Cys55, Cys100, Cys123, Cys136 and Cys 144 of SEQ ID NO: 3; and/or
2) His37, Cys38, Tyr39 of SEQ ID NO: 1 and His37, Cys38, Tyr39 of SEQ ID NO: 3; and/or
3) Asp50, Ala51, Glu52 and lys53 of SEQ ID NO: 1 and Asp50, Ala51, Glu52 and lys53 of SEQ ID NO: 3; and/or
4) Trp94 to Leu96 of SEQ ID NO: 1 and Trp94 to Leu96 of SEQ ID NO: 3.

18. The method of claim 1, said treatment causing the amelioration of symptoms associated with said neovascular disease or a reduction in pathological and excessive neoangiogenesis.

* * * * *

UNITED STATES PATENT AND TRADEMARK OFFICE
CERTIFICATE OF CORRECTION

PATENT NO. : 11,191,807 B2  
APPLICATION NO. : 16/468305  
DATED : December 7, 2021  
INVENTOR(S) : Xavier Guillonneau et al.

Page 1 of 1

It is certified that error appears in the above-identified patent and that said Letters Patent is hereby corrected as shown below:

In the Specification

Column 5,  
Line 11, "LCT (1 82 1, 500 μM)," should read --LCT (1μl, 500 μM),--.  
Line 47, "(E) Quantification" should read --Quantification--.

Signed and Sealed this  
Nineteenth Day of July, 2022

Katherine Kelly Vidal  
*Director of the United States Patent and Trademark Office*